(12) United States Patent
Farnet et al.

(10) Patent No.: US 7,257,562 B2
(45) Date of Patent: Aug. 14, 2007

(54) HIGH THROUGHPUT METHOD FOR DISCOVERY OF GENE CLUSTERS

(75) Inventors: Chris M. Farnet, Montreal (CA); Alfredo Staffa, Saint-Laurent (CA); Emmanuel Zazopoulos, Montreal (CA)

(73) Assignee: Thallion Pharmaceuticals Inc., Saint-Laurent, Quebec (CA)

( * ) Notice: Subject to any disclaimer, the term of this patent is extended or adjusted under 35 U.S.C. 154(b) by 224 days.

(21) Appl. No.: 10/232,370

(22) Filed: Sep. 3, 2002

(65) Prior Publication Data

US 2003/0138810 A1    Jul. 24, 2003

Related U.S. Application Data

(63) Continuation-in-part of application No. 10/205,032, filed on Jul. 26, 2002, now abandoned, said application No. 10/232,370 is a continuation-in-part of application No. 10/166,087, filed on Jun. 11, 2002, now Pat. No. 7,108,998, said application No. 10/232,370 is a continuation-in-part of application No. 10/152,886, filed on May 21, 2002, now Pat. No. 6,912,470, and a continuation-in-part of application No. 09/910,813, filed on Jul. 24, 2001, now abandoned, said application No. 10/232,370 is a continuation-in-part of application No. 10/132,134, filed on Apr. 26, 2002, now abandoned, said application No. 10/232,370 is a continuation-in-part of application No. 09/976,059, filed on Oct. 15, 2001, now Pat. No. 7,078,185.

(60) Provisional application No. 60/372,789, filed on Apr. 17, 2002, provisional application No. 60/342,133, filed on Dec. 26, 2001, provisional application No. 60/334,604, filed on Dec. 3, 2001, provisional application No. 60/307,629, filed on Jul. 26, 2001, provisional application No. 60/296,744, filed on Jun. 11, 2001, provisional application No. 60/291,959, filed on May 21, 2001, provisional application No. 60/286,346, filed on Apr. 26, 2001, provisional application No. 60/233,296, filed on Apr. 12, 2001, provisional application No. 60/239,924, filed on Oct. 13, 2000.

(51) Int. Cl.
 *G06N 3/00* (2006.01)
 *G01N 33/48* (2006.01)
 *C12Q 1/00* (2006.01)

(52) U.S. Cl. .............................. 706/13; 702/19; 435/4
(58) Field of Classification Search .................. 702/19, 702/22

See application file for complete search history.

(56) References Cited

U.S. PATENT DOCUMENTS

| | | | |
|---|---|---|---|
| 3,499,078 | A | 3/1970 | Luedemann et al. |
| 4,303,646 | A | 12/1981 | Cavalleri et al. |
| 5,716,849 | A | 2/1998 | Ligon et al. |
| 5,866,330 | A * | 2/1999 | Kinzler et al. ................. 435/6 |
| 6,090,601 | A | 7/2000 | Gustafsson et al. |
| 6,280,999 | B1 | 8/2001 | Gustafsson et al. |
| 6,492,161 | B1 * | 12/2002 | Hjorleifsdottir et al. . 435/235.1 |
| 6,524,841 | B1 | 2/2003 | McDaniel et al. |
| 6,551,795 | B1 | 4/2003 | Rubenfield et al. |
| 2003/0054353 | A1 | 3/2003 | Farnet et al. |

FOREIGN PATENT DOCUMENTS

| | | |
|---|---|---|
| CA | 2365904 | 9/2000 |
| CA | 2352451 | 10/2001 |
| WO | WO98/53097 | 11/1998 |
| WO | WO99/66028 | 12/1999 |
| WO | WO 00/31247 | 6/2000 |
| WO | WO 00/37608 | 6/2000 |
| WO | WO 00/53737 | 9/2000 |
| WO | WO 01/53533 | 7/2001 |

OTHER PUBLICATIONS

Dame et al., Molecular and Biochemical Parasitology, vol. 79, pp. 1-12, 1996.*
Gaisser et al., Journal of Bacteriology, vol. 179, pp. 6271-6278, 1997.*

Tomkins et al. Microbial & Comparative Genomics. vol. 4. 1999, pp. 203-217.*
Sleeman et al. Genomics, 2000, vol. 69, pp. 214-224.*
Marolda et al., Journal of Bacteriology. 1995, vol. 177, pp. 5539-5546.*
Gaisser et al. Journal of Bacteriology. 1997, vol. 179, pp. 6271-6278.*
Gudmundsdottir et al. Cloning and sequence analysis of the hemB gene of *Rhodothermus marinus.* Current Microbiology. vol. 39, 1999, p. 103-105.*
Srivatsan et al. Interstitial deletion of 11q13 sequences in HeLa cells. Genes, Chromosomes & Cancer. 2000, vol. 29, pp. 157-165.*
Velasco A. et al. (1998) J. of Bacteriology, vol. 180(5), pp. 1063-1071 "Genetic and Functionnal Analysis of the Styrene Catabolic Cluster of *Pseudomas* sp. Strain Y2".
Buchan A. et al. (2000) Appl. and Env. Microbiol., vol. 66(11), pp. 4662-4672 "Key Aromatic-Ring-Cleaving Enzyme, Protocatechuate 3,4-Dioxygenase, in the Ecologically Important Marine Roseobacter Lineage".
Masai E. et al. (1999) J. of Bacteriology, vol. 181(1), pp. 55-62 "Genetic and Biochemical Characterization of a 2-Pyrone-4,6-Dicarboxylic Acid Hydrolase Involved in the Protocatechuate 4,5-Cleavage Pathway of *Sphingomonas paucimobilis* SYK-6".
Ferrandez et al., J. of Biological Chemistry, vol. 273(40), pp. 25974-25986 "Catabolism of Phenylacetic Acid in *Escherichia coli*", 1998.
Schouten M. et al. (2001) Antimicrob Agent Chemother, vol. 45(3), pp. 986-989 "Molecular Analysis of Tu1546-Like Elements in Vancomycin-resistant *Enterococci* Isolated from Patients in Europe Shows Geographic Transposon Type Clustering".
Kuroda M. et al. (2001) The Lancet, vol. 357(9264), pp. 1225-1240 "Whole genome sequencing of meticilling-resistant *Staphylococcus aureus*".
Carniel E. (2001) Microbes Infect.,vol. 3(7), pp. 561-569 "The yersinia high-pathogenicity island: an iron-uptake island".
Nicholls L. et al. (2000) Mol. Microbiol, vol. 35(2), pp. 275-288 "Identificaiton of a novel genetic locus that is required for in vitro adhesion of a clinical isolate of enterohaemorrhagic *Escherichia coli* to epithelial cells".
Bentley S.D. et al. (2002) Nature, vol. 417 (6885), pp. 141-147 "Complete genome sequence of the model actinomycete *Streptomyces coelicolor* A3(2)".
Omura S. et al. (2001) Proc. Natl. Acad. Sci. USA, vol. 98, pp. 12215-12220 "Genome sequence of an industrial microorganism *Streptomyces avermitilis*: Deducing the ability of producing secondary metabolites".
Embley T.M. (1994) Annu. Rev. Microbiol., vol. 48, pp. 257-289 "The molecular phylogeny and systematics of the actinomycetes".
Altschul S.F. et al. (1999) J. Mol. Biol., Oct. 5; 215(3), pp. 403-410 "Basic Local Alignment Search Tool".
Altschul S.F. et al. (1997) Nucleic Acids Res., vol. 25 (17), pp. 3389-3402 "Grapped BLAST and PSI-BLAST: a new generation of protein database search programs".
Van Roey P. and Beerman T.A. (1989) Proc Natl Acad Sci USA, vol. 86, pp. 6587-6591 "Crystal structure analysis of auromomycin apoprotein (macromycin) shows importance of protein side chains to chromophore binding selectivity".
Fleishmann R.D. et al. (1995) Science, vol. 269, pp. 496-512 "Whole-Genome Random Sequencing and Assembly of *Haemophilus* influenza Rd".
Liu W. et al. (2002) Science, 297 (5584) pp. 1170-1173 "Biosynthesis of the enediyne antitumor antibiotic C-1027".
Stachelhaus T. et al. (1998) J. Biol. Chem., vol. 273 (35), pp. 22773-22781 "Peptide Bond Formation in Nonribosomal Peptide Biosynthesis".
Weinstein M. et al. (1964) Antimicrobial Agents and Chemotherapy, vol. 1964, pp. 24-32 "Everninomicin, a New Antibiotic Complex from *Micromonospora carbonacea*".
Tamura S. et al. (1963) Agr. Biol. Chem., vol. 27(8), pp. 576-582 "Isolation and Physiological Activities of Piericidin A, A Natural Insecticide Produced by *Streptomyces*".
Weymouth-Wilson A.C. (1997) NAt. Prod. Rep., pp. 99-110 "The role of carbohydrates in biologically active natural products".

Liu H. and Thorson J. (1994) Annu. Rev. Microbiol., vol. 48, pp. 223-256 "Pathways and mechanism in the biogenesis of novel deoxysugars by bacteria".
Hurley et al. (1975) J. Am. Chem. Soc., vol. 97(15), pp. 4372-4378 Biosynthesis of Anthramycin. Determination of the labelling pattern by the use of radioactive and stable isotope techniques.
Walczak et al., FEMS Microbiol Lett. 183 (2000):171-175 "Nonactin biosynthesis: the potential nonactin biosynthesis gene cluster contains type II polyketide synthase-like genes".
Jones and Hopwood, J. Biol. Chem. (1984), 259:14151-14157 "Molecular cloning and expression of the phenoxazinone synthase gene from *Streptomyces antibioticus*".
Suwa et al., 2000, Gene, 246:123-131 "Identification of two polyketide synthase gene clusters on the linear plasmid pSLA2-L in *Streptomyces rochei*".
Malpartida et al., 1987, Nature, 325:818-821 "Homology between *Streptomyces* genes coding for synthesis of different polyketides used to clone antibiotic biosynthetic genes".
Lombo et al., 1996, Gene, 172, 87-91 "Characterization of *Streptomyces argillaceus* genes encoding a polyketide synthase involved in the biosynthesis of the antitumor mithramycin".
Steffensky et al., 2000, Antimicrob. Agents Chemother, 44:1214-1222 "identification of the Novobiocin Biosynthetic Gene Cluster of *Streptomyces spheroides* NC1B 11891".
Strohl W.R., Metabolic Engineering 3(2000), 4-14 "Biochemical Engineering of Natural Products Biosyntehsis Pathways".
Smith et al., Nucleic Acids Research (1999) 27 No. 10:2145-2155 "The complete genome sequence of the *Streptomyces* themperate phage C31; evolutionary relatinships to other viruses".
Santi et al., 2000 Gene, 247:97-102 "An approach for obtaining perfect hybridization probes for unknown polyketide synthase genes: a search for the epothilone gene cluster".
Smulian et al., Genetics, vol. 157, Mar. 2001:991-1002 "The ste3 Pheronome Receptor Gene of *Pneumocystis carinii* is surrounded by a cluster of signal transduction genes".
Farnet C, Society for industrial Microbiology (SIM) presentation, San Diego CA, Jul. 24, 2000 "From genes to molecules: Genomics in natural product discovery and development".
Slides from Farnet presentation (C13) authorized for re-prensentation by Dr. William R. Strohl during plenary lecture entitled "Use of Bacterial Genomics in Drug Discovery" Feb. 2001, Mexico.
Arrowsmith et al., Mol Gen Genet. (1992) 234:254-264.
Hopwood, Chemical Reviews (1997)97:2465-2497.
Kunst et al., Nature (1997) 390:249-256.
Marahiel et al., Chem. Biol.(1997)4:561-567.
Marahiel et al., Chemical Reviews (1997)97:2651-2673.
Proctor et al., Fungal Genet Biol. (1999)27:100-112.
Schupp et al., J. Bacteriol (1995) 177:3673-3679.
Steller et al., Chem. Biol. (1999) 6:31-41.
Tsuge et al., Antimicrob Agents Chemother (1999)43:2183-2192.
Zazopoulos et al., Nature Biotechnology (2003)21:187-190.
Chen et al., (1999) Eur J. Biochem 261:98-107.
Piecq et al., (1994) DNA SEQ 4(4):219-229.
Cole S.T. and Saint-Girons, FEMS Microbial Rev. (1994) 14(2):139-60 "Bacteriol genomics".
Beyer et al., Biochem Biophys. Acta, (1999)1445:185-195 "Metabolic diversity in myxobacteria: identification of the myxalamid and the stimatellin biosynthetic gene cluster of stigmatella auratiaca SG a15 and a combined polyketide-(poly)peptide gene cluster from the epothilone producing strain *Sorangium cellulosum* So ce90".

* cited by examiner

*Primary Examiner*—John S. Brusca
*Assistant Examiner*—Russell S. Negin
(74) *Attorney, Agent, or Firm*—Nixon Peabody LLP; Mark J. FitzGerald

(57) ABSTRACT

A method for identifying gene cluster is disclosed. The method may be used for identifying gene clusters involved in the biosynthesis of natural products. A small insert library of DNA fragments of genomic DNA and a large insert library of DNA fragments of genomic DNA are prepared. Fragments in the small insert library are sequenced and compared by homology comparison under computer control to a database containing genes, gene fragments or proteins known to be involved in the biosynthesis of microbial natural products. Fragments having similar structure to genes, gene fragments or proteins known to be involved in the biosynthesis of naturally occurring metabolites are used as probes to screen the large insert library of genomic DNA to detect gene clusters involved in the biosynthesis of microbial natural products.

19 Claims, 5 Drawing Sheets

SEQUENCE LISTING

<160> NUMBER OF SEQ ID NOS: 1

<210> SEQ ID NO 1
<211> LENGTH: 7
<212> TYPE: PRT
<213> ORGANISM: Artificial sequence
<220> FEATURE:
<223> OTHER INFORMATION: Conserved active site motif in NRPS
      condensation domain.
<220> FEATURE:
<221> NAME/KEY: misc_feature
<222> LOCATION: (3)..(5)
<223> OTHER INFORMATION: Xaa can be any naturally occurring amino acid

<400> SEQUENCE: 1

His His Xaa Xaa Xaa Asp Gly
1               5

HIGH THROUGHPUT METHOD FOR DISCOVERY OF GENE CLUSTERS

This application is a continuation-in-part of U.S. Ser. No. 09/910,813 filed Jul. 24, 2001; and a continuation-in-part of U.S. Ser. No. 10/152,886 filed May 21, 2002, now U.S. Pat. No. 6,912,470, which claims benefit of provisional application 60/291,959 filed May 21, 2001 and U.S. Ser. No. 60/334,604 filed Dec. 3, 2001; and a continuation-in-part of U.S. Ser. No. 09/976,059 filed Oct. 15, 2001, now U.S. Pat. No. 7,078,185, which claims benefit of provisional applications 60/239,924 filed Oct. 13, 2000 and U.S. Ser. No. 60/283,296 filed Apr. 12, 2001; and a continuation-in-part of U.S. Ser. No. 10/205,032 filed Jul. 26, 2002 now abandoned which claims the benefit of provisional application U.S. Ser. No. 60/307,629, filed Jul. 26, 2001; and a continuation-in-part of U.S. Ser. No. 10/132,134 filed Apr.26, 2002 now abandoned which claims benefit of provisional application 60/286,346 filed Apr. 26, 2001; and a continuation-in-part of U.S. Ser. No. 10/166,087 filed Jun. 11, 2002 now U.S. Pat. No. 7,108,998, which claims benefit of provisional application U.S. Ser. No. 60/296,744 filed Jun. 11, 2001; each of which is hereby incorporated by reference in its entirety including any drawings, and from each of which priority is claimed. This application claims benefit under 35 USC 119 of provisional application U.S. Ser. No. 60/372,789 filed on Apr. 17, 2002 and of provisional application U.S. Ser. No. 60/342,133 filed on Dec. 26, 2001 which is also incorporated by reference in its entirety.

The invention relates to the fields of microbiology and genomics, and more particularly to a high-throughput method for discovery of gene clusters. The present invention allows rapid discovery of gene clusters involved in metabolic pathways or other processes.

BACKGROUND

Microbial genes whose products act in a coordinated fashion, for example a biosynthetic pathway, are often arranged in close physical proximity to one another in the organism's genome. Such genes are said to form a gene cluster. Gene clusters are involved in the biosynthesis of complex compounds, notably the biosynthesis of microbial natural products, and in the catabolism of complex compounds (e.g. Velasco et al., *J. of Bacteriology*, 180(5): 1063–1071; Buchan et al., *Appl. and Env. Microbiol.*, 66(11): 4662–4672; Masai et al., *J. of Bacteriology*, 181(1): 55–62; Ferrandez et al., *J. of Biological Chemistry*, 273(40), 25974–25986). Gene clusters may also provide resistance to therapeutic drugs (e.g. Schouten et al., *Antimicrob Agents Chemother*, 45(3):986–9). Gene clusters may constitute pathogenicity islands from various organisms (e.g. Kuroda et al., 357(9264):1225–40; Carniel E., *Microbes Infect.* 3(7):561–9; Nicholls et al., *Mol. Microbiol* 35(2):275–88).

Gene clusters are of significant interest in various fields. For example, gene clusters such as the Tn1546-like elements that are responsible for the spread of vancomycin resistance in clinical isolates of enterococci are of great interest to the medical field. The rapid identification of such clusters allows a better understanding of the spread and mechanisms of action of vancomycin resistance. Gene clusters for catabolic pathways are of interest in the field of bioremediation for the breakdown of toxic agents from contaminated environments and in the field of chemical engineering for the generation of economically valuable molecules from common, inexpensive materials. Gene clusters known as pathogenicity islands render otherwise harmless bacteria to highly pathogenic threats. For example, *E.coli* 0157 is a clinically important and often lethal pathogen that differs in part from the non-pathogenic *E. coli* K12 in that the former contains pathogenicity islands. Identification of such pathogenicity islands is of great importance to the medical field.

Natural product biosynthetic gene clusters are of significant interest in the field of combinatorial biosynthesis and metabolic engineering. Novel molecules may be made by genetic engineering of natural product biosynthetic genes. Improved methods to rapidly discover gene clusters involved in the biosynthesis of microbial natural products expands the repertoire of genes available for use in combinatorial biosynthesis and as biocatalysts and facilitates the discovery of new natural product molecules and variants of known molecules. The emergence of bacteria resistant to multiple antibiotics has led to renewed interest in isolating variants of known antibiotics and novel antibiotics, and also in identifying new genes and gene products that could serve as new targets for new or existing antibiotics.

Methods for natural product discovery have faced many challenges. Discovery efforts that focus on plant derived natural products are hampered by limited source material, typically low concentrations of active metabolite, difficulty extracting useful quantities of the natural product produced, and the fact that many secondary metabolic biosynthetic loci are expressed only under particular growth conditions (for example, pathogen infestation) that are poorly understood and may be difficult to reproduce experimentally. Discovery efforts that focus on microbial derived natural products are hampered by difficulties in cultivating the microbes; indeed most microbes have yet to be cultivated in vitro. In addition, many cultivated microorganisms are not amenable to fermentation. Furthermore many secondary metabolites are not expressed to detectable levels under in vitro conditions. Furthermore, natural products produced under in vitro conditions often vary according to the growth conditions, e.g. nutrients provided, and may not be representative of the full biosynthetic potential of the microorganism. Thus, there is a need for improved methods for discovery of gene clusters involved in the biosynthesis of natural products and for methods that do not require the cultivation, growth or fermentation of organisms.

Genome sequence of actinomycetes *S. coelicolor* (Bentley S. D. et al., *Nature*, 417, 141–147) and *S. avermitilis* (Omura S. et al., *Proc. Natl. Acad. Sci* USA 98, 12215–12220) has revealed the presence of numerous cryptic gene clusters encoding putative natural products, suggesting that well-studied strains may produce a greater number of bioactive compounds than has been detected by fermentation broth analyses. These cryptic gene clusters remain unexpressed until appropriate chemical or physical signals induce their expression. There is a need for a method of discovering gene clusters independently of expression of the genes forming the gene cluster or detection of their product.

Known methods of discovering gene clusters are often cluster-specific, and may not have broad application to smaller gene clusters or gene clusters encoding non-modular genes. In addition, many of these methods are labor-intensive, and involve sequencing significant amounts of DNA encoding genes that are not involved in the biosynthesis of the product of the target gene cluster. Because degenerate or universal probes or primers are often imperfect, natural product gene clusters may be missed. Furthermore, probes or primers may not reveal cryptic biosynthetic loci.

There is a continuing need for high throughput methods for identification of all gene clusters. There is also a need for methods for detecting natural product loci in a genome with minimal DNA sequencing, and in particular minimal sequencing of DNA encoding genes for primary metabolism. There is also a need for improved methods for detecting the biosynthetic loci for secondary metabolic pathways in an organism without having to sequence the entire genome of the organism. There is also a need for improved genomics-based methods for detecting gene clusters responsible for the biosynthesis of natural products in microbial organisms, which methods are rapid, use less reagents, are less labor-intensive, and are not dependent upon expression of the genes in the target gene clusters.

SUMMARY OF THE INVENTION

The invention involves a genome scanning method that combines random DNA sequencing followed by computer analysis of the DNA sequence. The genome scanning provides a method to rapidly search through the genome of a microorganism in order to discover gene clusters without having to sequence the entire genome. The method can be used to detect any cluster of genes that act together in a coordinated manner and are clustered together on a chromosome. In one embodiment, the method may be used to detect a gene cluster involved in the synthesis of a natural product. In another embodiment, the method may be used to detect a gene cluster involved in a catabolic pathway such as the degradation of phenolic compounds. In yet another embodiment, the method may be used to detect a gene cluster for a pathogenicity island from an organism. In yet another embodiment, the method may be used to detect a gene cluster that confers resistance to a natural product or drug.

In one embodiment, the organism is a known producer of a natural product, although the gene cluster responsible for production of the known natural product is unknown. In another embodiment, the organism is known to produce a particular natural product or multiple natural products but also contains a further gene cluster for the biosynthesis of natural products undetected by traditional methods. In another embodiment the organism is not known to produce a natural product. The genomes of many microorganisms contain multiple natural product biosynthetic loci and the present invention may be used to detect all natural product biosynthetic loci present in an organism's genome while minimizing the amount of DNA sequencing required.

DETAILED DESCRIPTION OF THE INVENTION

Figure 1:
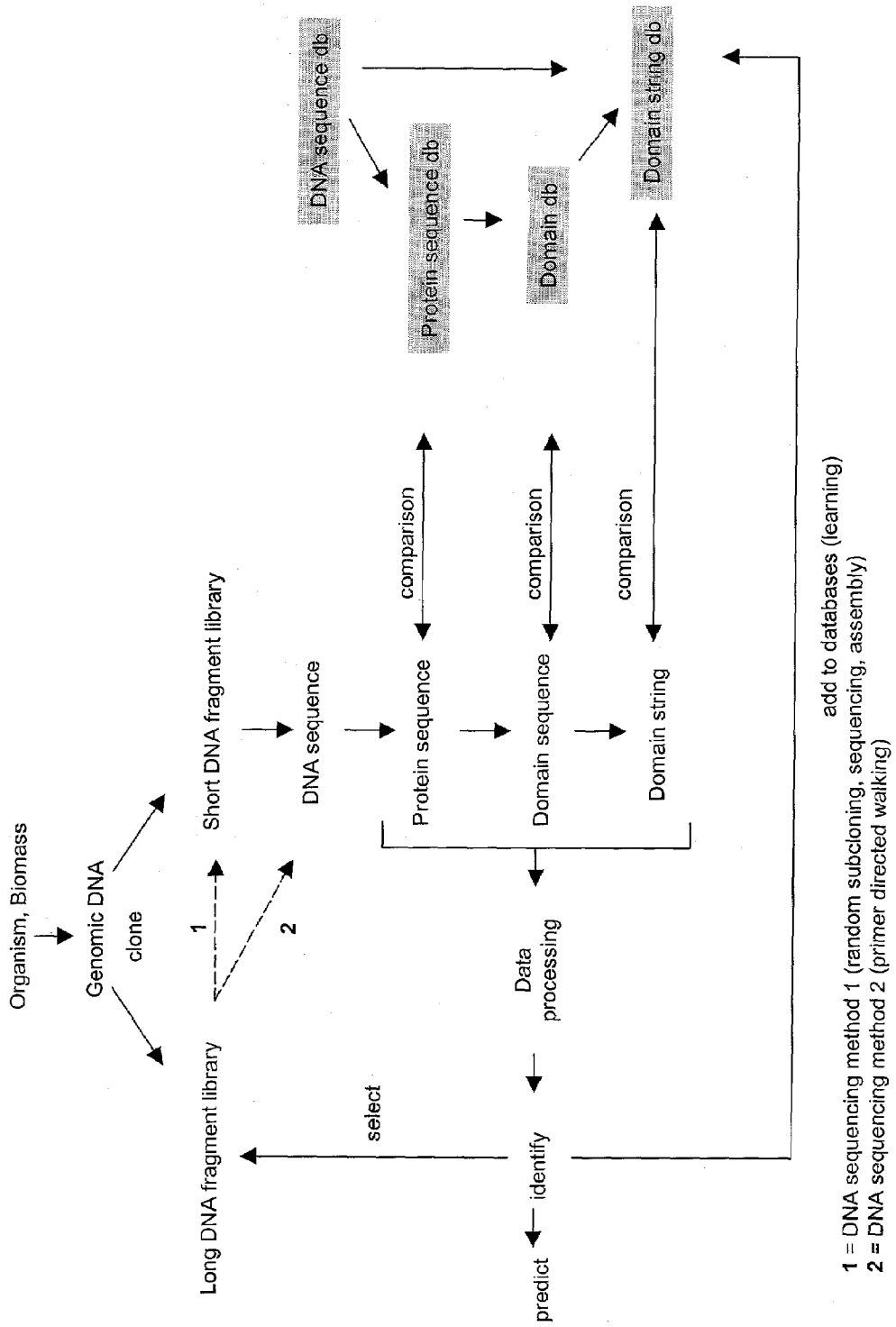
FIG. 1 is a schematic view of a method for discovery of a gene cluster according to one embodiment of the invention.

The meaning of target gene cluster, as used in the specification, refers to any group of two or more genes that act together in a coordinated manner and that are clustered together on a chromosome. The meaning of target gene cluster is not restricted to or associated with any particular type of metabolic pathway. Rather, the target gene cluster of the invention may be associated with a wide range of metabolic pathways or cellular processes including, but not limited to, the biosynthesis of natural products, the degradation of a compound, conferring resistance to therapeutic drugs, or pathogenicity islands from various organisms. A target gene cluster may be found in an organism not reported or known to contain the gene cluster.

The meaning of genome extends to all DNA contained within an organism, including naturally occurring plasmids or other episomal DNA, or in the case of eukaryotes, compartmentalized DNA.

Short, random genome sequence tags (GSTs) of about 700 base pairs are generated from a library of genomic DNA prepared from a microorganism. A GST, sometimes referred to as a "read", is DNA sequence information in computer-readable form so as to be compared with a database. GSTs derived from genes that are likely to be involved in the biosynthesis of natural products are identified by sequence comparisons to a database of microbial gene clusters known to be involved in natural product biosynthesis. Selected GSTs are then used to design screening probes to identify subgenomic fragments containing the genes of interest as well as the neighboring genes that may constitute a biosynthetic gene cluster.

Genome scanning provides an efficient way to discover natural product gene clusters as the analysis of a relatively small number of GSTs provides reasonable assurance of full genome representation. For example, analysis of 1,000 GSTs from a genome of 8.5 Mb (the approximate size of an actinomycete genome) provides DNA sequence coverage every 8.5 Kb (assuming random library coverage). Given that natural product gene clusters range in size between 20–200 Kb, it is expected that any given gene cluster will be represented by anywhere from two to more than twenty of 1,000 GSTs analyzed.

The genomic DNA may be derived from any prokaryotic or eukaryotic microorganism known or suspected to contain a gene cluster. The genomic DNA may be drawn from a population of uncultured microorganisms found in their natural habitat or environment or from biomass, thereby avoiding problems associated with cultivation and fermentation of microbes. The genomic DNA may also be derived from cultured microorganisms, either mixed or purified. A preferred source of the genomic DNA is microorganisms, such as bacteria and fungi. Bacterial species suitable for use in the method include substantially all bacterial species, both animal- and plant-pathogenic and nonpathogenic. Preferred microorganisms for the purpose of identifying natural product biosynthesis clusters include but are not limited to bacteria of the order Actinomycetales, also referred to as actinomycetes. Preferred genera of Actinomycetes include *Nocardia, Geodermatophilus, Actinoplanes, Micromonospora, Nocardioides, Saccharothrix, Amycolatopsis, Kutzneria, Saccharomonospora, Saccharopolyspora, Kitasatospora, Streptomyces, Microbispora, Streptosporangium, Actinomadura*. The taxonomy of actinomycetes is complex and reference is made to Goodfellow (1989) Suprageneric classification of actinomycetes, *Bergey's Manual of System-*

*atic Bacteriology,* Vol. 4, Williams and Wilkins, Baltimore, pp 2322–2339, and to Embley and Stackebrandt, (1994), The molecular phylogeny and systematics of the actinomycetes, *Annu. Rev. Microbiol.* 48, 257–289, for genera that may also be used with the present invention. One skilled in the art would understand that the preferred source of DNA will depend on the target gene cluster; e.g., actinomycetes, cyanobacteria, myxobacteria and bacilli for natural products, pseudomonads for catabolic pathways, etc.

The genomic DNA can be isolated from samples using various techniques well known in the art (*Nucleic Acids in the Environment Methods & Applications,* J. T. Trevors, D. D. van Elasas, Pringer Laboratory, 1995). Preferably, the genomic DNA obtained will be of high molecular weight and free of enzyme inhibitors and other contaminants. In a preferred embodiment, the size of the genomic DNA is of a molecular weight higher than 80 kb.

The genomic DNA is employed to produce at least one large-insert library. In some embodiments, the large insert library (sometimes referred to herein and in U.S. Ser. No. 09/910,813 as the cluster identification library or CIL), is used to generate a plurality of gene sequence tags (GSTs). A GST, sometimes referred to as a "read", is DNA sequence information in computer-readable form so as to be compared with a database. The GSTs generated are sometimes collectively referred to as a GST library and the sequence information of the GSTs is rendered in digital form as a GST database. The large insert library is further used to isolate the genes forming the gene cluster. In other embodiments, the genomic DNA is employed to produce at least one large insert library and at least one small insert library. The small insert library (sometimes referred to herein and in U.S. Ser. No. 09/910,813 as a genomic sampling library or GSL) is used to generate a plurality of GSTs. Reference to the GSTs, GST library, or GST database refers to the sequence information of the GSTs, whether the GSTs are generated from the large insert library or the small insert library. The large insert library is used to isolate the genes forming the gene cluster.

The recombinant DNA library or libraries may be prepared without prescreening the organism or population of organisms, cultured or not, for the presence of the target gene cluster. The genomic DNA fragments may be generated and subcloned into an appropriate cloning vector by a variety of procedures. Ideally, the genomic DNA fragments will be as random as possible. Mechanical shearing methods such as sonication, nebulization and the like, or passage through a fine needle with manual pressure are preferred methods, however enzymatic methods such as partial digestion with a frequently cutting restriction enzyme (for example Sau3AI or TaqI) and other methods can also be employed. When a mechanical shearing method is employed, the ends of such fragments may be "repaired" or blunted to generate uniform ends that can be enzymatically ligated to the appropriate restriction site(s) of the vector, either directly or with the use of DNA linkers. Smaller inserts are preferentially cloned.

Any conventional cloning vector, suitable for genomic DNA libraries, may be used including phage-derived vectors, plasmids, cosmids, phosmids, Bacterial Artificial Chromosomes (BACs), and Yeast Artificial Chromosomes (YACs). One skilled in the art will select an appropriate cloning vector based on the circumstances, e.g. typical plasmid cloning range of 0.1 to 10 kbp, typical cosmid cloning range 30 to 50 kbp, typical BAC cloning range 75–300 kbp etc. In general, the DNA sequence is inserted into an appropriate restriction endonuclease site(s) on the cloning vector by procedures known in the art. Such procedures and others are deemed to be within the scope of those skilled in the art.

In embodiments having both small insert library and a large insert library, probes derived from DNA sequences (GSTs) obtained from the small insert library are used to identify and isolate from the large insert library significantly larger genomic DNA fragments that include the probe together with its flanking sequences, and genes of the target gene cluster. The small insert library is formed of a population of randomly generated fragments so as to provide an adequate sampling of the entire DNA contained within a microorganism. Advantageously, the population includes fragments of all biosynthetic loci in the genome.

The small insert library of relatively short genomic DNA fragments is constructed. Preferably, the size of the DNA fragments forming the short insert sampling library will be substantially uniform. The actual size of the DNA fragments in the short insert library may vary, but the size must be of a length to provide sufficient sequence data to identify a fragment as part of the target gene cluster. In one embodiment of the invention, the size of the DNA fragments in the short insert library is about 1.5 kbp to about 10 kbp, in a preferred embodiment the size of the DNA fragments is about 1.5 kbp to about 5 kbp, in a more preferred embodiment the size of the DNA fragments is about 1.5 kbp to about 3 kbp. Since the current sequencing technology can routinely provide sequence information, referred to herein as a "read", of up to 700 bp, and sequencing can be carried out with primers flanking both sides of the insert, it is advantageous that the insert be at least the length of two reads so that each read yields different sequence data. The use of larger inserts increases the probability of obtaining intact genes together with required regulatory sequences that may be expressed in the cloning host, especially if the cloning host is closely related to the organism from which the genomic DNA was isolated. This may not be desirable as this may skew the population towards non-toxic or non-detrimental DNA fragments or beneficial DNA fragments.

DNA fragments forming the small insert library are cloned into an appropriate vector and serve as a source for genetic sampling. One suitable vector that may be used to prepare the small insert library is the pBluescript II™ cloning vector (Stratagene). Other suitable vectors include but are not limited to pUC19 and related vectors, Lambda vectors, M13 cloning vectors, pBR322 and related vectors.

Fragments from the small insert library are sequenced to provide Gene Sequence Tags (GSTs). The GSTs that correspond to fragments of the target gene cluster as determined by homology comparison with a database are used as probes to identify the large insert clone(s) containing the genes that form the target gene cluster.

Advantageously, the small insert library is as random as possible and its size, i.e. the number of individual clones, is large enough to provide an adequate representation of the DNA contained within the microorganism of interest. By estimating size of the target gene cluster and the size of the genome, a preferred library size may be determined. For example, the frequency of sequences containing genes from secondary metabolic pathways producing natural products in the small insert library reflects their occurrence in the genome. If the microorganism has one or more naturally occurring plasmids of moderate to high copy number, or has a genome that is segmented in a non-proportional fashion, the resulting small insert library will reflect this disproportionality. To overcome any bias that may arise due to such genetic disproportionality, a larger number of small insert clones may have to be processed and the size of the large insert library (i.e. number of clones) may likewise have to be increased under such circumstances. Alternatively, the chromosomal DNA may be purified away from non-chrosomal DNA by methods known in the art to overcome problems due to a high copy number of plasmids. In any event, the number of cloned DNA fragments in the short insert library or the library size must provide a reasonable probability that genes from the target gene cluster will be found in the representative fragments forming the short insert library.

A large insert library of relatively long DNA fragments is constructed. The DNA fragments forming the large insert library are cloned into an appropriate vector and serve as a screening library from which the target gene cluster(s) is/are obtained. The large insert library may also serve as a source for GSTs by sequencing the ends of the inserts. Suitable vector systems for use in preparing the large insert library include but are not restricted to Lambda vectors such as Lambda DASH II, cosmid vectors such as pWE15 or SuperCos-1™, P1 cloning vectors such as pAd10sacBII, fosmid vectors such as pFos1, Bacterial Artificial Chromosome (BAC) vectors such as pBeloBAC11, and Yeast Artificial Chromosomes (YAC) vectors such as pYAC4. The vector is selected to be stably propagated in an appropriate host. The short insert library and the large insert library need not be prepared in the same host organism, i.e., *E. coli, Bacillus, Saccharomyces cerevisiae*, human cell lines, etc., may be used.

Preferably, the size of the genomic DNA fragments in the large insert library will be substantially uniform. The size of the genomic DNA fragments in the large insert library will vary widely depending on the vector system used. In the case where a cosmid vector system is employed, the size of the DNA fragment in the large-insert library is about 30 kbp to about 50 kbp.

Where the genomic DNA is isolated from a purified organism, an appropriate number of the large insert clones is one that allows several-fold coverage of the genome of interest. Where the DNA is isolated from a mixed population of organisms, the number of large insert clones should preferably be larger so as to maximize the probability to find overlapping clones.

Short lengths of DNA from either end of cloned inserts in the short insert library and/or the target insert library are sequenced using a forward primer (F) or a reverse primer (R) to provide a plurality of Gene Sequence Tags (GSTs). In one embodiment, a GST is produced from each of the cloned inserts in the short insert library. In embodiments having a single large-insert library, the GSTs are generated from the large insert library, for example by sequencing a number of ends from the fragments in the large insert library. In other embodiments GSTs produced from a small insert library are supplemented with sequences produced from the large insert library. The length of the GST sequence will depend on the sequencing technology used but typically ranges from about 300 bp with a traditional (manual) DNA sequencing apparatus up to about 700 bp or more with an automated DNA sequencer such as an a 3700 ABI capillary electrophoresis DNA sequencer (Applied Biosystems). In one embodiment the GSTs are about 700 base pairs in length.

The sequence of each GST is provided in computer readable form for in silico screening of a database containing genes, gene fragments or DNA known to be involved in the target gene cluster. In one embodiment the in silico screening is based on the nucleic acid sequence of the GSTs. In a preferred embodiment, the nucleic acid sequence of the GST is translated to its corresponding amino acid sequence, and the in silico screening is based on the comparison of amino acid sequences of the GSTs against a database containing proteins or protein fragments known to be involved in the target gene cluster. Advantageously, translation of the nucleic acid sequence of the GSTs to their corresponding amino acid sequence or of a database of genes, gene fragments and DNA to the corresponding amino acid sequences is computer-assisted.

The nucleic acid sequence or the amino acid sequence of the GSTs, in computer readable form, is compared under computer control using publicly available bioinformatics tools such as BLAST, Prodom, Clustal, etc. to a DNA or protein database containing genes, gene fragments, or clusters of genes, or their corresponding protein products known to be involved in the target gene cluster. The database may be a public gene database such as GenBank, EMBL, or a private database. A preferred database for the identification of natural product biosynthetic genes is the DECIPHER™ database of microbial genes (Ecopia BioSciences Inc., St.-Laurent, Quebec).

Advantageously, the reference database used for homology comparison contains at least one or preferably multiple homologues of one or more genes of the target gene cluster. A homologous amino acid sequence is one that differs from an amino acid sequence by one or more conservative amino acid substitutions. Such a sequence encompasses allelic variants, as well as sequences containing deletions or insertions that retain the functional characteristics of the polypeptide. Homologous amino acid sequences include sequences that are identical or substantially identical to the amino acid sequence. By amino acid sequence substantially identical is meant a sequence that differs from the sequence of reference by a majority of conservative amino acid substitutions. Conservative amino acid substitutions are substitutions among amino acids of the same class. These classes include, for example, amino acids having uncharged polar side chains, such as asparagine, glutamine, serine, threonine, and tyrosine; amino acids having basic side chains, such as lysine, arginine, and histidine; amino acids having acidic side chains, such as aspartic acid and glutamic acid; and amino acids having nonpolar side chains, such as glycine, alanine, valine, leucine, isoleucine, proline, phenylalanine, methionine, trytophan, and cysteine.

Homology comparison of the GSTs and the sequences in the database may be assessed by percent identity or by E value. The E value relates the expected number of chance alignments with an alignment score at least equal to the observed alignment score. An E value of 0.00 indicates a perfect homolog. The E values are calculated as described in Altschul et al. J. Mol. Biol., October 5; 215(3) 403–10, the teachings of which are incorporated herein by reference. The E value assists in the determination of whether two sequences display sufficient similarity to justify an inference of homology. An E value of $10^{-10}$ will generally be indicative of two proteins that are significantly related to one another, an E value of $10^{-15}$ being especially significant. However the length and accuracy of the sequenced being compared with the database will strongly influence the value of E considered significant. The use of a filter to mask stretches of low complexity or highly biased amino acid sequences can be used to increase the specificity of homology comparisons.

Comparison of sequences may also be assessed by Clustal alignments showing conserved positions between the sequences encoded by the GSTs and the sequences of the database. In this manner, GSTs likely to belong to genes involved in the target gene cluster are identified. Amino acid sequences are aligned to maximize identity. Gaps may be artificially introduced into the sequence to attain proper alignment. Once the optimal alignment has been set up, the degree of homology is established by recording all of the positions in which the amino acid of both sequences are identical, relative to the total number of positions.

Clones that contain a GST that encode a similar primary amino acid sequence based on homology comparison with gene fragments known to be involved in the target gene cluster are sequenced from the short insert library and/or the large insert library. In a preferred embodiment, the DNA clone from the small insert library that corresponds to a GST of interest can be sequenced from the other end using a universal reverse primer and analyzed for homology to the reference database. Sequencing at the opposite end of the insert from which the GST was derived identifies clones whose inserts contain GSTs that correspond to gene fragments known to be involved in the target gene cluster at both ends of a single short insert. In another embodiment, the DNA clone from the large insert library that corresponds to a GST of interest can be sequenced from the other end using a universal reverse primer and analyzed for homology to the reference database, thereby identifying clones whose inserts contain GSTs that correspond to gene fragments known to be involved in the target gene cluster at both ends of the insert. Insert clones that display homology to the target gene cluster at both ends are likely to contain sequences from the target gene cluster. Identification of clones having homology to the target gene cluster requires the presence of characterized homologues in the reference database.

The GSTs that correspond to genes or gene fragments known to be involved in the target gene cluster are used to derive hybridization probes to isolate the corresponding DNA fragments in the large insert library (referred to as the large insert clones) by standard hybridization procedures on high density array matrices such as nylon membranes or DNA microchips. Such hybridization probes can be nucleic acids, DNA or RNA, containing a sequence from the GST, in full or in part, that is labeled either with a radioisotope such as $^{32}P$ or with a non-radioactive detection system such as digoxygenin (Roche). With organisms whose genome is highly biased in that it is highly GC-rich or AT-rich, larger probes can lead to non-specific hybridization or background. Therefore, for GC-rich organisms such as actinomycetes relatively short oligonucleotide probes of approximately 20 nucleotides are preferred over longer PCR-amplified fragments. In the event that the desired gene cluster extends beyond the boundaries of a large insert clone or a series of overlapping large insert clones, the DNA sequence at these boundaries can be used to design additional probes which can be used in another round of hybridization to identify other overlapping large insert clones. This second round of hybridization can be performed at any stage of detection and cloning of the target gene cluster from the large insert library or final assembly of the target gene cluster.

The insert of the large insert clone is entirely sequenced by any method known in the art. In one embodiment, the insert of the large insert clone is sequenced by a shotgun DNA sequencing technique. In other embodiments, the insert of the large insert clone is sequenced by a technique selected from a subcloning technique, a primer walking technique, and a nested deletion technique.

The sequences of the large insert clone are then assembled and the open reading frames are identified using appropriate methods known to one skilled in the art. These methods or criteria for gene identification can vary depending on the nature of the organism from which the genomic DNA was isolated. Overlapping large insert clones can be assembled together using computer algorithms to generate a large, contiguous DNA contig sequence or multiple DNA contig sequences that are separated by relatively small gaps. One skilled in the art can then analyze these contigs of DNA sequence using bioinformatics tools to identify the open reading frames and regulatory sequences. The sequences are assembled into the target gene cluster by additional computer analysis. The sequences of the DNA contigs and the proteins which they are predicted to encode can then be submitted to appropriate databases.

Figure 2:
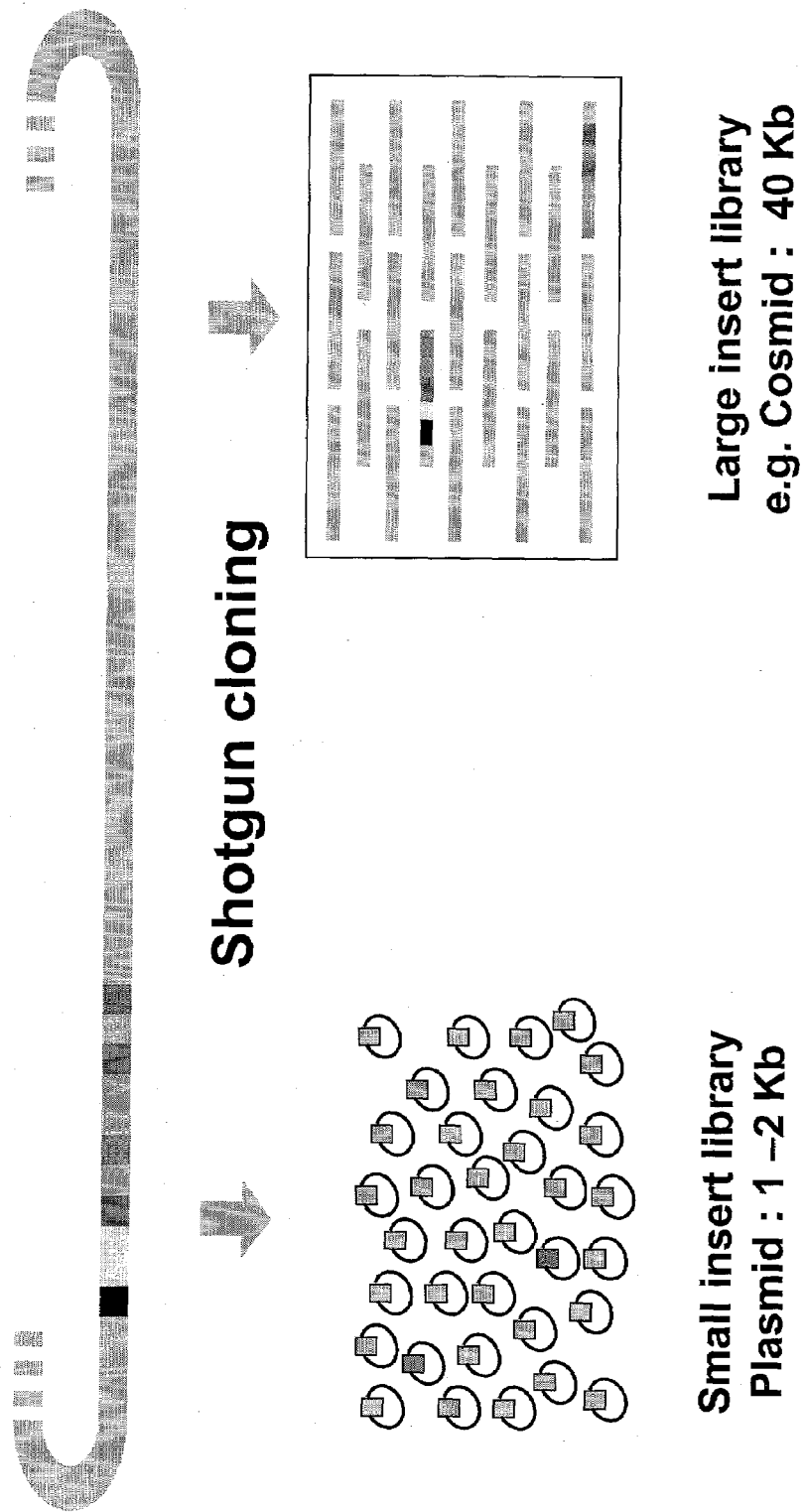
FIG. 2 illustrates construction of a small insert library and a large insert library according to the method of FIG. 1.
Figure 3:
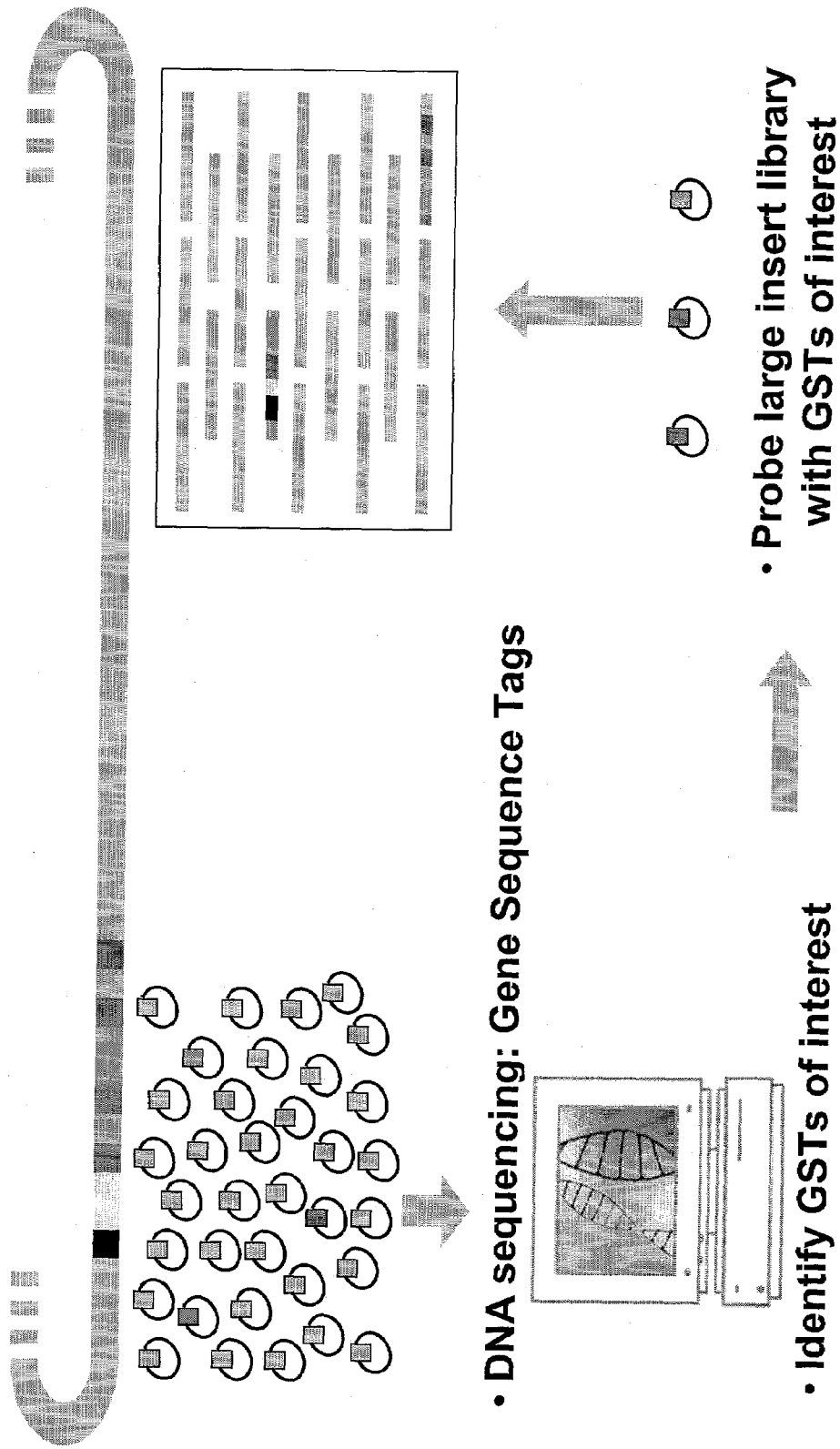
FIG. 3 illustrates selection of Gene Sequence Tags (GSTs) from the small insert library for use of probes for screening the large insert library according to the method of FIG. 1.
Figure 4:
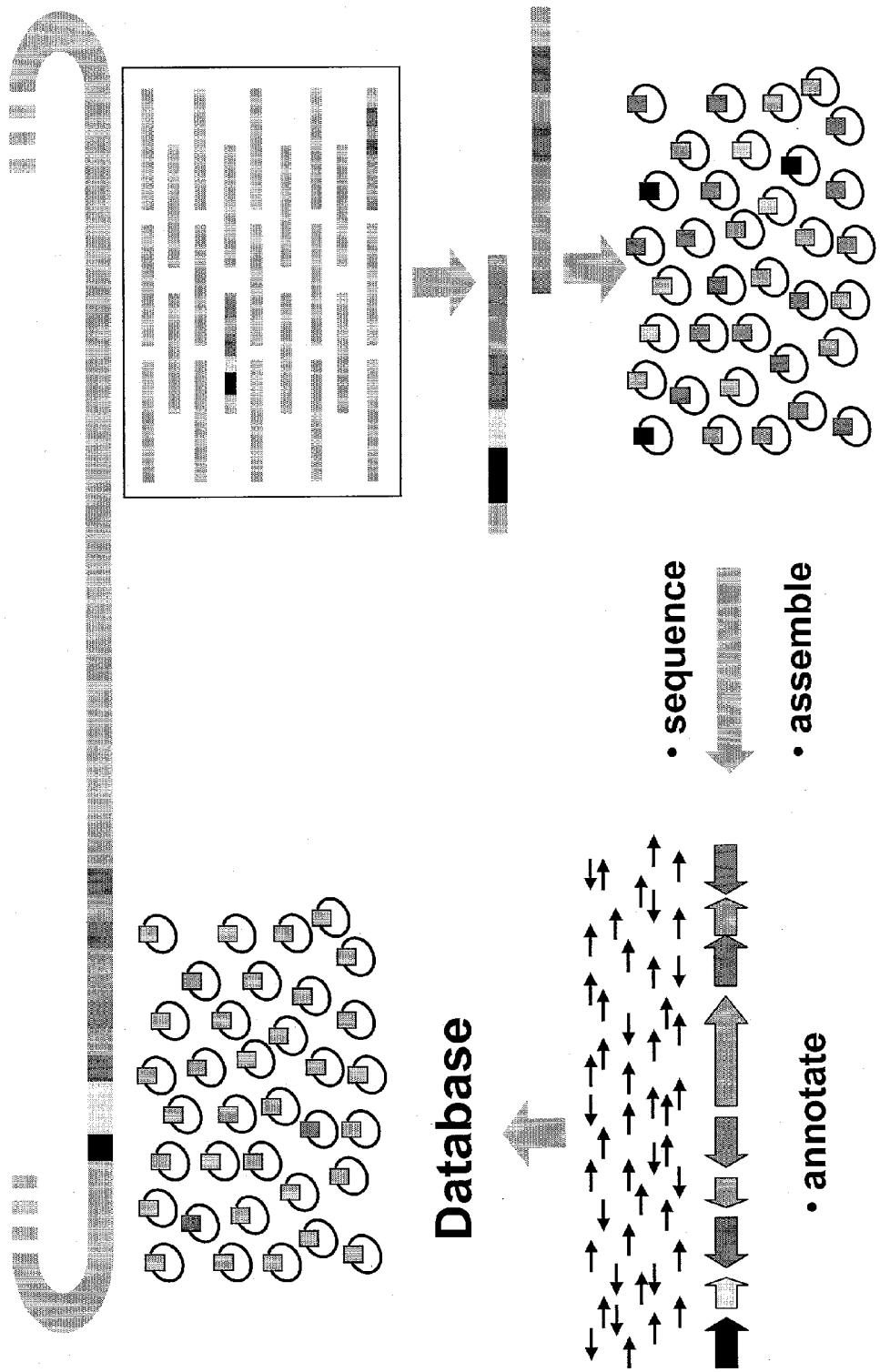
FIG. 4 illustrates identification and cloning of the gene cluster from the large-insert library according to the method of FIG. 1.
Figure 5:
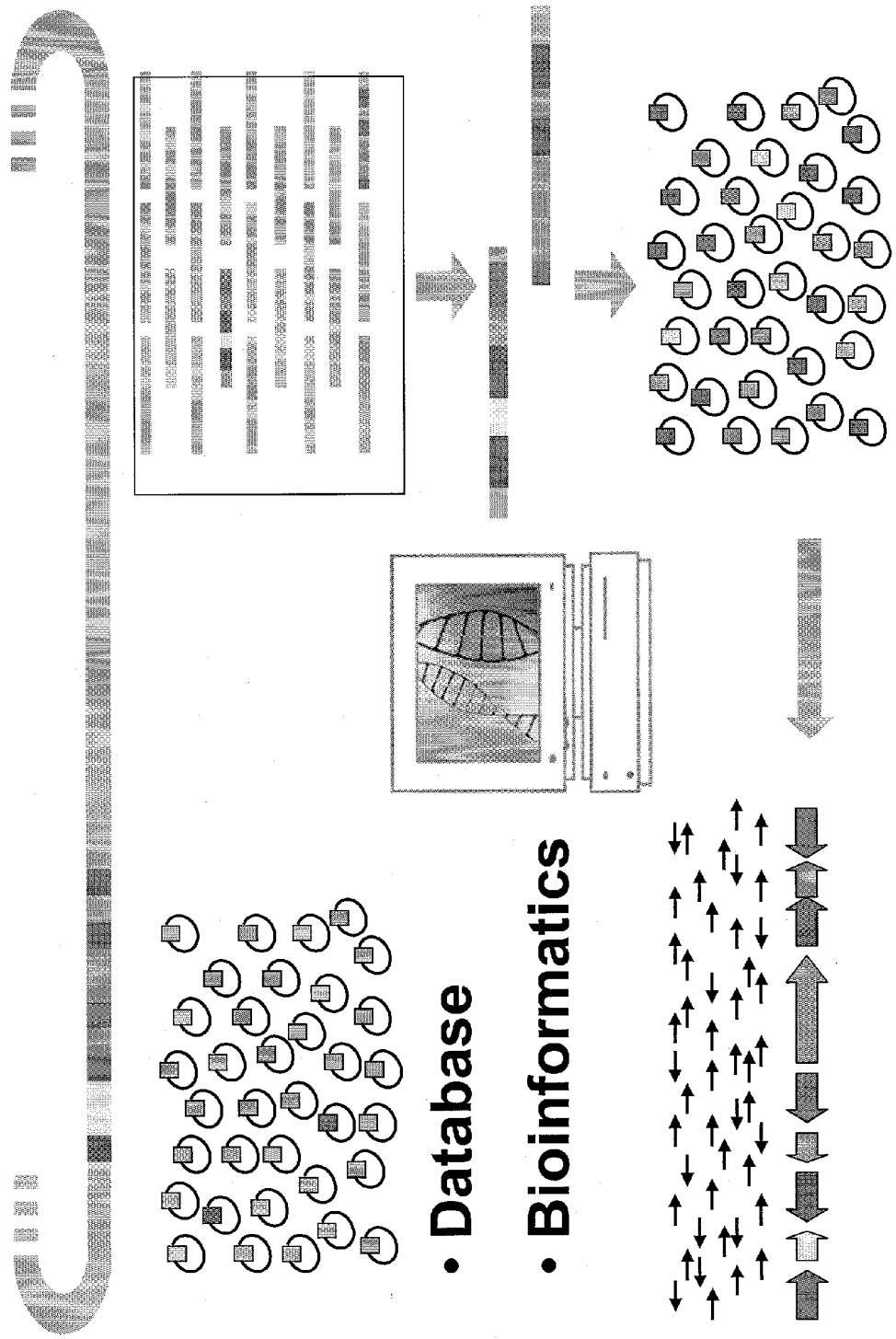
FIG. 5 illustrates the assembly of the contigs of DNA sequence into a target gene cluster by computer analysis and the submission of the DNA contigs and the proteins which they are predicted to encode into a database.

Reviewing the method by reference to the figures, high molecular weight genomic DNA of interest is isolated from a cell mass or biomass (FIG. 1). A small insert library and a large insert library are constructed so as to contain randomly generated fragments of DNA (FIG. 2). The small insert library is composed of individual clones each containing a piece of genomic DNA insert in the range of 1.5–3 kb carried on a cloning vector that can be propagated in a suitable host organism. The large insert library is composed of individual clones each containing a piece of genomic DNA of interest that is at least 30 kb carried on a cloning vector that can be propagated in a suitable host organism. The small insert library serves as a source for genomic DNA sampling and is sequenced to generate Gene Sequence Tags (GSTs) as illustrated in FIG. 3. Alternatively the GST may be produced by sequencing the ends of the inserts in the large library. Computer-assisted analysis of the GSTs identifies those GSTs likely to reside within the target gene cluster (GSTs of interest). Molecular probe(s) are then designed from the GSTs of interest and are used to identify, by nucleic acid hybridization, the clones in the large insert library that contain the probe(s). Once identified, the large insert clone(s) of interest are sequenced by a shotgun method similar to that employed on genomic DNA for the generation of the small insert library (FIG. 4). A sufficient number of shotgun sequences are done so as to allow for computer-assisted reconstruction or assembly of the entire sequence of the large insert clone(s).

The invention may be used to discover natural product biosynthetic loci for a wide variety of types of natural products, including non-ribosomal peptides, lipopeptides, orthosomycins, polyketides, polyethers, enediynes, and benzodiazepines. The invention has been used to discover and distinguish between variations of natural products within these groups, for example the method can be used to discover and distinguish glycolipopeptides and acidic lipopeptides, or to discover and distinguish avilamycin-type orthosomycins and everninomycin-type orthosomycins (see Table 1). The invention has been used to discover natural products biosynthetic loci of a particular class, wherein the genes involved in the biosynthesis have an unconventional organization or structure as compared with the structure or organization of known genes associated with the class, for example unusual polyketide synthases genes (see Table 1).

The invention has been used to discover the biosynthetic locus associated with a product from an organism known to produce the product of the locus, as well as to discover cryptic biosynthetic loci, i.e. biosynthetic loci associated with a product that the organism was not previously reported or known to produce (see Table 1).

Table 1 outlines a number of microbial natural product biosynthetic loci discovered by the high throughput method. The first column ("Organism") lists the name of the organism studied and the corresponding collection number; a cross-section of microbial genera are represented, including *Actinoplanes, Streptomyces, Micromonospora, Amycolatopsis, Kitasatosporia, Kutzneria, Geodermatophilus, Saccharothrix,* and *Actinomadura*. The second column ("No. of GSTs") lists the number of forward reads that were compared by Blast analysis to reference sequence databases. The third column ("Locus") lists the name of the biosynthetic locus or gene cluster discovered. The fourth column ("Type of Natural Product") describes the nature of the natural product produced by the locus or gene cluster discovered. The fifth column ("Probe derived from GST homologous to") describes the proposed function of the polypeptide encoded by the GST from which the probe used to identify cosmid clones of interest was derived. The sixth column ("Locus Size") lists the length in kilobases of the sequenced portion of the locus or cluster. The seventh column ("No. of Overlapping Cosmids") lists the number of overlapping cosmid clones that were sequenced for each locus. The eighth column ("No. of GSTs in Locus") lists the number of forward read GSTs that were retroactively mapped to the sequenced portion of each locus. The ninth column ("Kb/GST") is the value obtained by dividing column six by column eight which reflects the average distance between GSTs.

TABLE 1

Summary of selected loci discovered by the high throughput method

| | Organism | No. of GSTs | Locus | Type of Natural Product | Probe derived from GST homologous to: | Locus Size (Kb)* | No. of Overlapping Cosmids*** | No. of GSTs in Locus | Kb/GST |
|---|---|---|---|---|---|---|---|---|---|
| 1 | *Actinoplanes* sp. ATCC 33076 | 930 | Ramoplanin | glycolipopeptide | NRPS | 88 | 6 | 6 | 14.7 |
| 2 | *Streptomyces mobaraensis* NRRL B-3729 | 450 | Avilamycin-like | avilamycin-type orthosomycin | dTDP-glucose 4,6-dehydratase | 51 | 2 | 4 | 12.8 |
|  |  |  | Monensin-like | glycosylated polyether | type I PKS | 124 | 7 | 5 | 24.8 |
|  |  |  | Unknown peptide/ Piericidin | peptide + polyketide | NRPS | 120 | 6 | 5 | 24.0 |
| 3 | *Streptomyces refuineus* subsp. *thermotolerans* NRRL-3143 | 671 | Anthramycin | benzodiazepine; small NRPS | NRPS/amino acid oxidase | 60 | 2 | 8 | 7.5 |
|  |  |  | 024A** | acidic lipopeptide | NRPS | 53 | 2 | 5 | 10.6 |
| 4 | *Micromonospora carbonacea* var. *aurantiaca* NRRL 2997 | 508 | Everninomicin | everninomicin; orthosomycin | various sugar metabolism genes | 70 | 3 | 7 | 10.0 |
|  |  |  | Rosaramicin | glycosylated polyketide | type I PKS | 95 | 4 | 9 | 10.6 |
| 5 | *Micromonospora echinospora* subsp. *calichensis* NRRL 15839 | 669 | Calicheamicin | enediyne | O-methyltransferase | 130 | 10 | 6 | 21.7 |
| 6 | *Streptomyces aizunensis* NRRL B-11277 | 462 | prophage*** | not a "natural product" | phiC31 gp9a | 35 | 1 | 2 | 17.5 |
|  |  |  |  |  | phiC31 gp33 & gp35 | 32 | 1 | 5 | 6.4 |
| 7 | *Amycolatopsis orientalis* ATCC 43491 | 1261 | 007A | enediyne | transmembrane efflux protein | 103 | 5 | 12 | 8.6 |
| 8 | *Kitasatosporia setae* NRRL B-16185 | 480 | 033C** | unusual polyketide | unusual PKS | 63 | 2 | 1 | 63.0 |
| 9 | *Kutzneria viridogrisea* NRRL B-24059 | 480 | Sporaviridin | glycosylated polyketide | type I PKS & dNDP-glucose synthase | 171 | 6 | 7 | 24.4 |
| 10 | *Geodermatophilus obscurus* NRRL B-3577 | 576 | 035A | aromatic polyketide | type II PKS cyclase + cytochrome P450 | 76 | 3 | 2 | 38.0 |
| 11 | *Saccharothrix aerocolonigenes* ATCC 39243 | 1038 | 132H | enediyne + polyketide | type I PKS | 116 | 3 | 7 | 16.6 |
| 12 | *Actinomadura* sp. ATCC 39334 | 1152 | 153A** | lipopeptide | NRPS | 74 | 4 | 5 | 14.8 |
| 13 | *Streptomyces platensis* NRRL 18993 | 1536 | Dorrigocins/ Migrastatin | unusual polyketides | unusual PKS | 54 | 3 | 7 | 7.7 |
|  | Avg: | 485 |  |  |  | Avg: 84 | 4 | 6 | 18.5 |

Loci in BOLD were expected to be present in the genome of the given organism; not all sequenced loci are listed for the given organism; NRSP, non-ribosomal peptide synthase; PKS, polyketide synthase
*size of sequenced overlapping cosmid clones including some flanking primary metabolism genes
**locus incomplete
***two non-overlapping cosmid clones
***at least this many cosmid clones overlap in the given locus

EXAMPLES

Example 1

Use of Genome Scanning to Identify Enediyne Biosynthetic Loci From Known Enediyne-producing Microorganisms and From Organisms not Previously Reported to Produce Enediyne Natural Products

Macromomycin is a chromoprotein enediyne produced by *Streptomyces macromyceticus* (NRRL B-5335). *Streptomyces macromyceticus* (NRRL B-5335) was obtained from the Agricultural Research Service collection (National Center for Agricultural Utilization Research, 1815 N. University Street, Peoria, Ill. 61604) and cultured using standard microbiological techniques (Kieser et al., *Practical Streptomyces Genetics,* John Innes Center, Norwich Research Park, Colney, Norwich NR4 6UH England, 2000). The organism was propagated on oatmeal agar medium at 28 degrees Celsius for several days. For isolation of high molecular weight genomic DNA, cell mass from three freshly grown, near confluent 100 mm petri dishes was used. The cell mass was collected by gentle scraping with a plastic spatula. Residual agar medium was removed by repeated washes with STE buffer (75 mM NaCl; 20 mM Tris-HCl, pH 8.0; 25 mM EDTA). High molecular weight DNA was isolated by established protocols and its integrity was verified by field inversion gel electrophoresis (FIGE) using the preset program number 6 of the FIGE MAPPER™ power supply (BIORAD). This high molecular weight genomic DNA was used to prepare a small insert library, and a large insert library.

For the generation of a small insert library, genomic DNA was randomly sheared by sonication. DNA fragments having a size range between 1.5 and 3 kb were fractionated on an agarose gel and isolated using standard molecular biology techniques (Sambrook et al., supra). The ends of the obtained DNA fragments were repaired using T4 DNA polymerase (Roche) as described by the supplier. The repaired DNA fragments were subcloned into a derivative of pBluescript SK+ vector (Stratagene) which does not allow transcription of cloned DNA fragments. This vector was selected as it contains a convenient polylinker region surrounded by sequences corresponding to universal sequencing primers such as T3, T7, SK, and KS (Stratagene). The EcoRV restriction site found in the polylinker region was used as it allows insertion of blunt-end DNA fragments. Ligation of the inserts, use of the ligation products to transform *E. coli* DH10B (Invitrogen) host and selection for recombinant clones were performed as previously described (Sambrook et al., supra). Plasmid DNA carrying the *S. macromyceticus* genomic DNA fragments was extracted by the alkaline lysis method (Sambrook et al., supra) and the insert size of 1.5 to 3 kb was confirmed by electrophoresis on agarose gels A large insert library was constructed from the *S. macromyceticus* high molecular weight genomic DNA using the SuperCos-1 cosmid vector (Stratagene™). The cosmid arms were prepared as specified by the manufacturer. The high molecular weight DNA was subjected to partial digestion at 37 degrees Celsius with approximately one unit of Sau3AI restriction enzyme (New England Biolabs) per 100 micrograms of DNA in the buffer supplied by the manufacturer. This enzyme generates random fragments of DNA ranging from the initial undigested size of the DNA to short fragments of which the length is dependent upon the frequency of the enzyme DNA recognition site in the genome and the extent of the DNA digestion. At various timepoints, aliquots of the digestion were transferred to new microfuge tubes and the enzyme was inactivated by adding a final concentration of 10 mM EDTA and 0.1% SDS. Aliquots judged by FIGE analysis to contain a significant fraction of DNA in the desired size range (30–50 kb) were pooled, extracted with phenol/chloroform (1:1 vol:vol), and pelletted by ethanol precipitation.

The 5' ends of Sau3AI DNA fragments were dephosphorylated using alkaline phosphatase (Roche) according to the manufacturer's specifications at 37 degrees Celcius for 30 min. The phosphatase was heat inactivated at 70 degrees Celcius for 10 min and the DNA was extracted with phenol/chloroform (1:1 vol:vol), pelletted by ethanol precipitation, and resuspended in sterile water. The dephosphorylated Sau3AI DNA fragments were then ligated overnight at room temperature to the SuperCos-1 cosmid arms in a reaction containing approximately four-fold molar excess SuperCos-1 cosmid arms.

The ligation products were packaged using Gigapack® III XL packaging extracts (Stratagene™) according to the manufacturer's specifications. The large insert library consisted of 864 isolated cosmid clones in *E. coli* DH10B (Invitrogen). These clones were picked and inoculated into nine 96-well microtiter plates containing LB broth (per liter of water: 10.0 g NaCl; 10.0 g tryptone; 5.0 g yeast extract) which were grown overnight and then adjusted to contain a final concentration of 25% glycerol. These microtiter plates were stored at –80 degrees Celcius and served as glycerol stocks of the large insert library. Duplicate microtiter plates were arrayed onto nylon membranes as follows. Cultures grown on microtiter plates were concentrated by pelleting and resuspending in a small volume of LB broth. A 3×3 96-pin-grid was spotted onto nylon membranes.

The membranes, representing the complete large insert library, were then layered onto LB agar and incubated overnight at 37 degrees Celcius to allow the colonies to grow. The membranes were layered onto filter paper pre-soaked with 0.5 N NaOH/1.5 M NaCl for 10 min to denature the DNA and then neutralized by transferring onto filter paper pre-soaked with 0.5 M Tris (pH 8)/1.5 M NaCl for 10 min. Cell debris was gently scraped off with a plastic spatula and the DNA was crosslinked onto the membranes by UV irradiation using a GS GENE LINKER™ UV Chamber (BIORAD). Considering an average size of 8 Mb for an actinomycete genome and an average size of 35 kb of genomic insert in the large insert library, this library represents roughly a 4-fold coverage of the microorganism's entire genome.

The small insert library was analyzed by sequence determination of the cloned genomic DNA inserts. The universal primers KS or T7, referred to as forward (F) primers, were used to initiate polymerization of labeled DNA. Extension of at least 700 bp from the priming site were achieved using the TF, BDT v2.0 sequencing kit as specified by the supplier (Applied Biosystems). Sequence analysis of the small genomic DNA fragments to generate a database of DNA sequence reads or GSTs was performed using a 3700 ABI capillary electrophoresis DNA sequencer (Applied Biosystems). The average length of the DNA sequence reads (i.e. the GSTs) was about 700 base pairs. Further analysis of the GSTs generated was performed by sequence homology comparison to various protein sequence databases. The DNA sequences of the obtained GSTs were translated into amino acid sequences and compared to the National Center for Biotechnology Information (NCBI) nonredundant protein database and the DECIPHER™ database (Ecopia Bio-Sciences Inc., St.-Laurent, Quebec, CANADA) using the BLASTP algorithm with the default parameters (Altschul, S. F. et al. Gapped BLAST nd PSI-BLAST: a new generation of protein database search programs, *Nucleic Acids Res.*, 25, 3389–3402 1997). Sequence similarity with known proteins of defined function in the database provided a means to identify proteins indicative of an enediyne biosynthetic loci based on the function of the partial protein that is encoded by the translated GST.

A total of 479 GSTs obtained with the forward sequencing primer were analyzed by sequence comparison. These GSTs were supplemented with an additional 179 GSTs produced by sequencing the ends of inserts of clones in the large insert library, for a total of 658 GSTs. Sequence alignments displaying an E value of at least e-5 were considered as significantly homologous and retained for further evaluation. GSTs showing similarity to a gene of interest were selected and used to identify larger segments of genomic DNA from the large insert library that include the gene(s) of interest. Several *S. macromyceticus* GSTs that contained genes of interest were pursued. One of these GSTs encoded a portion of an oxidoreductase based on BLAST analysis of the forward read and a portion of the macromomycin apoprotein based on Blast analysis of the reverse read and the apoprotein component has been well characterized (Van Roey and Beerman (1989) Proc Natl Acad Sci USA Vol. 86 pp. 6587–6591). Oligonucleotide probes derived from such GSTs were used to screen the large insert library and the resulting positive cosmid clones were sequenced. Overlapping cosmid clones provided in excess of 125 kb of sequence information surrounding the macromomycin apoprotein gene.

Hybridization oligonucleotide probes were radiolabeled with $P^{32}$ using T4 polynucleotide kinase (New England Biolabs) in 15 microliter reactions containing 5 picomoles of oligonucleotide and 6.6 picomoles of $[\gamma\text{-}P^{32}]$ATP in the kinase reaction buffer supplied by the manufacturer. After 1 hour at 37 degrees Celcius, the kinase reaction was terminated by the addition of EDTA to a final concentration of 5 mM. The specific activity of the radiolabeled oligonucleotide probes was estimated using a Model 3 Geiger counter (Ludlum Measurements Inc., Sweetwater, Tex.) with a built-in integrator feature. The radiolabeled oligonucleotide probes were heat-denatured by incubation at 85 degrees Celcius for 10 minutes and quick-cooled in an ice bath immediately prior to use.

The *S. macromyceticus* large insert library membranes were pretreated by incubation for at least 2 hours at 42 degrees Celcius in Prehyb Solution (6×SSC; 20 mM $NaH_2PO_4$; 5× Denhardt's; 0.4% SDS; 0.1 mg/ml sonicated, denatured salmon sperm DNA) using a hybridization oven with gentle rotation. The membranes were then placed in Hyb Solution (6×SSC; 20 mM $NaH_2PO_4$; 0.4% SDS; 0.1 mg/ml sonicated, denatured salmon sperm DNA) containing $1\times10^6$ cpm/ml of radiolabeled oligonucleotide probe and incubated overnight at 42 degrees Celcius using a hybridization oven with gentle rotation. The next day, the membranes were washed with Wash Buffer (6×SSC, 0.1% SDS) for 45 minutes each at 46, 48, and 50 degrees Celcius using a hybridization oven with gentle rotation. The *S. macromyceticus* large insert library membranes were then exposed to X-ray film to visualize and identify the positive cosmid clones. Positive clones were identified, cosmid DNA was extracted from 30 ml cultures using the alkaline lysis method (Sambrook et al., supra) and the inserts were entirely sequenced using a shotgun sequencing approach (Fleischmann et al., (1995) *Science*, 269:496–512).

Sequencing reads were assembled using the Phred-Phrap™ algorithm (University of Washington, Seattle, USA) recreating the entire DNA sequence of the cosmid insert. Reiterations of hybridizations of the large insert library with probes derived from the ends of the original cosmid allowed indefinite extension of sequence information on both sides of the original cosmid sequence until the complete target gene cluster was obtained. An unusual polyketide synthase (designated herein as PKSE) was found approximately 40 kb upstream of the macromomycin apoprotein gene. No other polyketide synthase or fatty acid synthase gene cluster was found in the vicinity of the macromomycin apoprotein gene. Four other genes subsequently found to be enediyne-specific genes are clustered with or are in close proximity to the PKSE gene in the macromomycin biosynthetic locus and are designated herein as TEBC, UNBL, UNBV, and UNBU. These enediyne-specific genes and proteins (PKSE, TEBC, UNBL, UNBV and UNBU) are described in greater detail in U.S. Ser. No. 10/152,996. Table 2 lists the results of sequence comparison using the Blast algorithm (Altschul et al., supra) for each of these enediyne-specific polypeptides from the macromomycin locus.

TABLE 2

| Family | #aa | GenBank homology Accession, #aa | probability | identity | similarity | proposed function of GenBank match |
|---|---|---|---|---|---|---|
| PKSE | 1936 | T37056, 2082aa | 6e–86 | 273/897 (30.43%) | 372/897 (41.47%) | multi-domain beta keto-acyl synthase, *Streptomyces coelicolor* |
|  |  | NP_485686.1, 1263aa | 5e–82 | 256/900 (28.44%) | 388/900 (43.11%) | heterocyst glycolipid synthase, *Nostoc* sp |
|  |  | AAL01060.1, 2573aa | 6e–78 | 244/884 (27.6%) | 376/884 (42.53%) | polyunsaturated fatty acid synthase, *Photobacterium profundum* |
| TEBC1 | 162 | NP_249659.1, 148aa | 4e–06 | 38/134 (28.36%) | 59/134 (44.03%) | hypothetical protein, *Pseudomonas aeruginosa* |
|  |  | CAB50777.1, 150aa | 4e–06 | 39/145 (26.9%) | 65/145 (44.83%) | hypothetical protein, *Pseudomonas putida* |
|  |  | NP_214031.1, 128aa | 2e–04 | 33/129 (25.58%) | 55/129 (42.64%) | hypothetical protein, *Aquifex aeolicus* |
| TEBC2 | 157 | NP_242865.1, 138aa | 0.27 | 31/131 (23%) | 50/131 (37%) | 4-hydroxybenzoyl-CoA thioesterase, *Bacillus halodurans* |
| UNBL | 327 | NP_422192.1, 423aa | 0.095 | 30/86 (34.88%) | 40/86 (46.51%) | peptidase, *Caulobacter crescentus* |
| UNBV | 642 | NO HOMOLOG |  |  |  |  |
| UNBU | 433 | NP_486037.1, 300aa | 1e–06 | 49/179 (27.37%) | 83/179 (46.37%) | hypothetical protein, *Nostoc* sp. |
|  |  | NP_107088.1, 503aa | 2e–04 | 72/280 (25.71%) | 126/280 (45%) | hypothetical protein, *Mesorhizobium loti* |

TABLE 2-continued

| Family | #aa | GenBank homology Accession, #aa | probability | identity | similarity | proposed function of GenBank match |
|---|---|---|---|---|---|---|
| | | NP_440874.1, 285aa | 4e−04 | 47/193 (24.35%) | 86/193 (44.56%) | hypothetical protein, *Synechocystis* sp |

The invention was also used to identify the non-chromoprotein enediyne calicheamicin produced by *Micromonospora echinospora* subsp. *calichensis* NRRL 15839. A small insert library and a large insert library of *M. echinospora* genomic DNA were prepared as described above. A total of 288 small insert library clones were sequenced with the forward primer. These GSTs were supplemented with an additional 381 GSTs produced by sequencing clones in the large insert library, for a total of 669 GSTs. The GSTs were analyzed by sequence comparison using the BLASTP algorithm with the default parameters (Altschul et al., supra) to identify those clones that contained inserts related to the enediyne biosynthetic genes, particularly PKSE, TEBC, UNBL, UNBV and UNBU. Such GST clones were identified and were used to isolate or identify cosmid clones from the *M. echinospora* large insert library. Overlapping cosmid clones were sequenced and assembled as described above. The resulting DNA sequence information was more than 125 kilobases in length and included the calicheamicin genes described in WO 00/37608. The calicheamicin biosynthetic genes disclosed in WO 00/37608 represent a partial biosynthetic locus and do not disclose the unusual PKS gene (PKSE) and four other flanking genes (UNBL, UNBV, UNBU, and TEBC) that are homologuous to those in the macromomycin biosynthetic locus. Table 3 lists the results of sequence comparison using the BLASTP algorithm with the default parameters (Altschul et al., supra) for each of these enediyne-specific polypeptides from the calicheamicin locus.

large insert cluster identification library. Both libraries contained randomly fragmented genomic DNA and were therefore representative of the entire genome. For the generation of the small insert library, genomic DNA was sonicated and fragments of 1.5 to 3 kb were prepared by agarose gel electrophoresis before cloning into plasmid vectors. For the generation of the large insert library, genomic DNA was fragmented to a size range of 30 to 50 kb by partial digestion with the restriction endonuclease Sau3A1 before cloning into cosmid vectors. One thousand GSTs (average read length, 700 bp) were obtained from the small insert library, translated into amino acid sequence and compared to the DECIPHER™ database (Ecopia BioSciences Inc., St.-Laurent, Quebec, CANADA) using the BLASTP algorithm with the default parameters (Altschul et al, supra) to identify gene sequences likely to be involved in the production of enediyne natural products, in particular the endiyne-specific polypeptides PKSE, TEBC, UNBL, UNBV and UNBU (unpublished manuscript).

Selected gene sequences from the GSTs were used to design screening probes to identify cosmids containing putative natural product gene clusters from the large insert library. Selected cosmids were sequenced by shotgun sequencing, and overlapping cosmids were identified by using the cosmid end sequences as probes to screen the large insert library.

TABLE 3

| Family | #aa | GenBank homology Accession, #aa | probability | identity | similarity | proposed function of GenBank match |
|---|---|---|---|---|---|---|
| PKSE | 1919 | AAF26923.1, 2439aa | 1e−60 | 228/876 (26.03%) | 317/876 (36.19%) | polyketide synthase, *Polyangium cellulosum* |
| | | NP_485686.1, 1263aa | 5e−59 | 148/461 (32.1%) | 210/461 (45.55%) | heterocyst glycolipid synthase, *Nostoc* sp |
| | | T37056, 2082aa | 9e−58 | 161/466 (34.55%) | 213/466 (45.71%) | multi-domain beta keto-acyl synthase, *Streptomyces coelicolor* |
| TEBC | 148 | NP_249659.1, 148aa | 8e−06 | 41/133 (30.83%) | 62/133 (46.62%) | hypothetical protein, *Pseudomonas aeruginosa* |
| | | AAD49752.1, 148aa | 1e−05 | 41/138 (29.71%) | 63/138 (45.65%) | orf1, *Pseudomonas aeruginosa* |
| | | NP_242865.1, 138aa | 2e−04 | 32/130 (24.62%) | 56/130 (43.08%) | 4-hydroxybenzoyl-CoA thioesterase, *Bacillus halodurans* |
| UNBL | 322 | NO HOMOLOG | | | | |
| UNBV | 651 | NO HOMOLOG | | | | |
| UNBU | 321 | NP_486037.1, 300aa | 8e−09 | 61/210 (29.05%) | 99/210 (47.14%) | hypothetical protein, *Nostoc* sp |
| | | NP_107088.1, 503aa | 5e−05 | 58/208 (27.88%) | 96/208 (46.15%) | hypothetical protein, *Mesorhizobium loti* |

The invention was also used to identify the biosynthetic locus for dynemicin from the known dynemicin-producer *Micromonospora chersina* strain M956-1, ATCC 53710 using the procedures described above in regard to *Streptomyces macromyceticus*. High molecular weight genomic DNA was prepared from the *M. chersina* organism and used to generate a small insert genomic sampling library and a The invention was also used to isolate enediyne natural product biosynthetic loci from actinomycete strains not reported to produce enediynes. Genomic DNA from *Streptomyces ghanaensis* NRRL B-12104 was prepared according to procedures described above. *S. ghanaensis* had not previously been described to produce enediyne compounds. A small insert library and a large insert library of *S. ghanaensis* genomic DNA were prepared as described above. A total of 435 small library clones were sequenced with the forward primer. An additional 203 GSTs were produced by sequencing clones in the large insert library, for a total of 638 GSTs. The GSTs were analyzed by sequence comparison using the BLASTP algorithm with the default parameters (Altschul et al., supra). Surprisingly, two GSTs from S. ghanaensis were identified as encoding portions of genes in the 5-gene cassette common to the macromomycin, calicheamicin and dynemicin enediyne biosynthetic loci. One of these GSTs encoded a portion of a TEBC homologue and the other encoded a portion of a UNBV homologue. These GSTs were subsequently found in a putative enediynes biosynthetic locus in S. ghanaensis. As in the macromomycin, calicheamicin and dynemicin enediyne biosynthetic loci, the UNBV and TEBC genes were found to flank a PKSE gene and are adjacent to UNBL and UNBU genes. The putative enediyne locus included a gene encoding a homologue of the macromomycin apoprotein approximately 50 kb downstream of the UNBV-UNBU-UNBL-PKSE-TEBC cassette. The presence of the 5-gene cassette in the vicinity of an apoprotein suggests that putative enediyne locus in S. ghanaensis represents a biosynthetic locus for an unknown chromoprotein enediyne that was not previously described to be produced by S. ghanaensis NRRL B-12104. Table 4 lists the results of sequence comparison using the Blast algorithm for each of the enediyne-specific polypeptides from the putative locus.

The genomic sampling method using the procedures described in regards to S. macromyceticus was applied to genomic DNA from Amycolatopsis orientalis ATCC 43491. A. orientalis has not previously been described to produce enediyne compounds. A small insert library and a large insert library of A. orientalis genomic DNA were prepared. A total of 1025 small insert library clones were sequenced with the forward primer and an additional 236 GSTs were produced from the large insert library for a total of 1261 GSTs. The GSTs were analyzed by sequence comparison using the BLASTP algorithm with the default parameter (Altschul et al., supra). Several secondary metabolism loci were identified and sequenced. One of these loci included a 5-gene cassette common to all enediyne biosynthetic loci. The A. orientalis genome also contains an enediyne apoprotein gene that is similar to that from the macromomycin and 009C loci as well as other chromoprotein enediynes. Therefore, A. orientalis, the producer of the well-known glycopeptide antibiotic vancomycin, has the genomic potential to produce a chromoprotein enediyne. Table 5 lists the results of sequence comparison using the BLASTP algo-

TABLE 4

| Family | #aa | GenBank homology Accession, #aa | probability | identity | similarity | proposed function of GenBank match |
|---|---|---|---|---|---|---|
| PKSE | 1956 | T37056, 2082aa | 1e–101 | 298/902 (33.04%) | 395/902 (43.79%) | multi-domain beta keto-acyl synthase, Streptomyces coelicolor |
|  |  | NP_485686.1, 1263aa | 2e–99 | 274/900 (30.44%) | 407/900 (45.22%) | heterocyst glycolipid synthase, Nostoc sp. |
|  |  | BAB69208.1, 2365aa | 3e–89 | 282/880 (32.05%) | 366/880 (41.59%) | polyketide synthase, Streptomyces avermitilis |
| TEBC | 152 | NP_249659.1, 148aa | 5e–07 | 39/131 (29.77%) | 59/131 (45.04%) | hypothetical protein, Pseudomonas aeruginosa |
|  |  | NP_231474.1, 155aa | 2e–04 | 30/129 (23.26%) | 62/129 (48.06%) | hypothetical protein, Vibrio cholerae |
|  |  | NP_214031.1, 128aa | 2e–04 | 31/128 (24.22%) | 55/128 (42.97%) | hypothetical protein, Aquifex aeolicus |
| UNBL | 329 | NO HOMOLOG |  |  |  |  |
| UNBV | 636 | NP_615809.1, 2275aa | 6e–05 | 72/314 (22.93%) | 114/314 (36.31%) | cell surface protein, Methanosarcina acetivorans |
| UNBU | 382 | NP_486037.1, 300aa | 4e–07 | 46/175 (26.29%) | 81/175 (46.29%) | hypothetical protein, Nostoc sp |
|  |  | NP_107088.1, 503aa | 6e–06 | 68/255 (26.67%) | 118/255 (46.27%) | hypothetical protein, Mesorhizobium loti | rithm for each of the enediyne-specific polypeptides from the putative chromoprotein enediyne from A. orientalis.

TABLE 5

| Family | #aa | GenBank homology Accession, #aa | probability | identity | similarity | proposed function of GenBank match |
|---|---|---|---|---|---|---|
| PKSE | 1939 | T37056, 2082aa | 5e–96 | 291/906 (32.12%) | 399/906 (44.04%) | multi-domain beta keto-acyl synthase, Streptomyces coelicolor |
|  |  | NP_485686.1, 1263aa | 9e–87 | 255/897 (28.43%) | 395/897 (44.04%) | heterocyst glycolipid synthase, Nostoc sp. |
|  |  | BAB69208.1, 2365aa | 8e–86 | 285/926 (30.78%) | 393/926 (42.44%) | modular polyketide synthase, Streptomyces avermitilis |
| TEBC | 146 | NP_214031.1, 128aa | 0.052 | 28/124 (22.58%) | 51/124 (41.13%) | hypothetical protein, Aquifex aeolicus |
| UNBL | 324 | NO HOMOLOG |  |  |  |  |
| UNBV | 654 | NP_618575.1, 1881aa | 0.001 | 80/332 (24.1%) | 117/332 (35.24%) | cell surface protein, Methanosarcina acetivorans |
| UNBU | 329 | NP_486037.1, 300aa | 0.005 | 56/245 (22.86%) | 96/245 (39.18%) | hypothetical protein, Nostoc sp |

The genomic sampling method using the procedures described in regards to *S. macromyceticus* was applied to genomic DNA from *Kitasatosporia* sp. CECT 4991. This organism was not previously described to produce enediyne compounds. A small insert library and a large insert library of genomic DNA libraries from *Kitasatosporia* sp. were prepared. A total of 1390 small insert library clones were sequenced with the forward primer and an additional 169 GSTs were produced from the large insert library for a total of 1559 GSTs. The GSTs were analyzed by sequence comparison using the BLASTP algorithm with the default parameters (Altschul et al., supra). Surprisingly, two GSTs from *Kitasatosporia* sp. were identified as encoding portions of genes in the 5-gene cassette common to enediyne biosynthetic loci. One of these GSTs encoded a portion of a PKSE homologue and the other encoded a portion of a UNBV homologue. These *Kitasatosporia* sp. GSTs were subsequently found in a putative enediyne genetic locus which includes a 5-gene cassette common to all enediyne biosynthetic loci. Therefore, *Kitasatosporia* sp. CECT 4991 has the genomic potential to produce enediyne compound(s). Table 6 lists the results of sequence comparison using the BLASTP algorithm for each of the enediyne-specific polypeptides from the putative enediyne locus from *Kitasatosporia* sp.

The genomic sampling method using the procedures described in regards to *S. macromyceticus* was applied to genomic *Micromonospora megalomicea* NRRL 3275. This organism was not previously described to produce enediyne compounds. A small insert library and a large insert library of genomic DNA from *M. megalomicea* were prepared. A total of 1390 small insert library clones were sequenced with the forward primer and analyzed by sequence comparison using the BLASTP algorithm with the default parameters (Altschul et al., supra). Surprisingly, one GST from *M. megalomicea* was identified as encoding a portion of the PKSE gene present in the 5-gene cassette common to enediyne biosynthetic loci. The forward read of this GST encoded the C-terminal portion of the KS domain and the N-terminal portion of the AT domain of a PKSE gene. The complement of the reverse read of this GST encoded the C-terminal portion of the AT domain of a PKSE gene. This *M. megalomicea* GST was subsequently found in a putative enediyne locus which includes a 5-gene cassette common to all enediyne biosynthetic loci. Therefore, *M. megalomicea* has the genetic potential to produce enediyne compound(s). Table 7 lists the results of sequence comparison using the BLASTP algorithm for each of the enediyne-specific polypeptides from the putative enediyne-locus from *M. megalomiceas*.

TABLE 6

| Family | #aa | GenBank homology Accession, #aa | probability | identity | similarity | proposed function of GenBank match |
|---|---|---|---|---|---|---|
| PKSE | 1958 | BAB69208.1, 2365aa | 1e−81 | 273/926 (29.48%) | 354/926 (38.23%) | polyketide synthase, *Streptomyces avermitilis* |
| | | T37056, 2082aa | 3e−78 | 263/895 (29.39%) | 356/895 (39.78%) | multi-domain beta keto-acyl synthase, *Streptomyces coelicolor* |
| | | NP_485686.1, 1263aa | 7e−71 | 231/875 (26.4%) | 345/875 (39.43%) | heterocyst glycolipid synthase, *Nostoc* sp. |
| TEBC | 158 | NP_249659.1, 148aa | 1e−04 | 38/133 (28.57%) | 61/133 (45.86%) | hypothetical protein, *Pseudomonas aeruginosa* |
| | | AAD49752.1, 148aa | 3e−04 | 38/138 (27.54%) | 62/138 (44.93%) | orf1, *Pseudomonas aeruginosa* |
| | | NP_231474.1, 155aa | 7e−04 | 31/127 (24.41%) | 61/127 (48.03%) | hypothetical protein, *Vibrio cholerae* |
| UNBL | 327 | NO HOMOLOG | | | | |
| UNBV | 676 | NO HOMOLOG | | | | |
| UNBU | 338 | NP_486037.1, 300aa | 5e−08 | 66/240 (27.5%) | 105/240 (43.75%) | hypothetical protein, *Nostoc* sp |
| | | NP_440874.1, 285aa | 2e−04 | 51/190 (26.84%) | 98/190 (51.58%) | hypothetical protein, *Synechocystis* sp. |

TABLE 7

| Family | #aa | GenBank homology Accession, #aa | probability | identity | similarity | proposed function of GenBank match |
|---|---|---|---|---|---|---|
| PKSE | 1927 | NP_485686.1, 1263aa | 3e−76 | 247/886 (27.88%) | 365/886 (41.2%) | heterocyst glycolipid synthase, *Nostoc* sp |
| | | T37056, 2082aa | 3e−75 | 269/903 (29.79%) | 354/903 (39.2%) | multi-domain beta keto-acyl synthase, *Streptomyces coelicolor* |
| | | BAB69208.1, 2365aa | 9e−74 | 277/923 (30.01%) | 359/923 (38.89%) | polyketide synthase, *Streptomyces avermitilis* |
| TEBC | 154 | NP_249659.1, 148aa | 2e−06 | 43/147 (29.25%) | 66/147 (44.9%) | hypothetical protein, *Pseudomonas aeruginosa* |
| | | AAD49752.1, 148aa | 2e−05 | 42/147 (28.57%) | 65/147 (44.22%) | orf1, *Pseudomonas aeruginosa* |
| | | CAB50777.1, 150aa | 1e−04 | 40/139 (28.78%) | 61/139 (43.88%) | hypothetical protein, *Pseudomonas putida* |
| UNBL | 322 | NO HOMOLOG | | | | |
| UNBV | 659 | CAC44518.1, 706aa | 0.048 | 50/166 (30.12%) | 67/166 (40.36%) | putative secreted esterase, *Streptomyces coelicolor* |
| UNBU | 354 | NP_486037.1, 300aa | 5e−06 | 66/268 (24.63%) | 118/268 (44.03%) | hypothetical protein, *Nostoc* sp |

The genomic sampling method using the procedures described in regards to *S. macromyceticus* was applied to genomic DNA from *Saccharothrix aerocolonigenes* ATCC 39243. This organism was not previously described to produce enediyne compounds. A small insert library and a large insert library of genomic DNA from *Saccharothrix aerocolonigenes* were prepared. A total of 513 small insert library clones were sequenced with the forward primer and an additional 525 GSTs were produced by sequencing clones in the large insert library, for a total of 1038 GSTs. The GSTs were analyzed by sequence comparison using the BLASTP algorithm with the default parameters (Altschul et al., supra). Several secondary metabolism loci were identified and sequenced. One of these loci is a putative enediyne locus and includes the 5-gene cassette common to all enediyne biosynthetic loci. Therefore, *Saccharothrix aerocolonigenes* has the genetic potential to produce enediyne compound(s). Table 8 lists the results of sequence comparison using the BLASTP algorithm for each of these enediyne-specific polypeptides from the putative enediyne locus from *Saccharothrix aerocolonigenes*.

TABLE 8

| Family | #aa | GenBank homology Accession, #aa | probability | identity | similarity | proposed function of GenBank match |
|---|---|---|---|---|---|---|
| PKSE | 1892 | BAB69208.1, 2365aa | 1e−108 | 312/872 (35.78%) | 404/872 (46.33%) | polyketide synthase, *Streptomyces avermitilis* |
|  |  | T37056, 2082aa | 1e−101 | 290/886 (32.73%) | 407/886 (45.94%) | multi-domain beta keto-acyl synthase, *Streptomyces coelicolor* |
|  |  | T30183, 2756aa | 4e−94 | 271/886 (30.59%) | 398/886 (44.92%) | hypothetical protein, *Shewanella* sp. |
| TEBC | 143 | NP_442358.1, 138aa | 0.001 | 32/127 (25.2%) | 48/127 (37.8%) | hypothetical protein, *Synechocystis* sp. |
| UNBL | 313 | NO HOMOLOG |  |  |  |  |
| UNBV | 647 | AAD34550.1, 1529aa | 0.012 | 76/304 (25%) | 105/304 (34.54%) | esterase, *Aspergillus terreus* |
| UNBU | 336 | NP_486037.1, 300aa | 1e−04 | 42/172 (24.42%) | 79/172 (45.93%) | hypothetical protein, *Nostoc* sp. |
|  |  | NP_440874.1, 285aa | 1e−04 | 48/181 (26.52%) | 90/181 (49.72%) | hypothetical protein, *Synechocystis* sp. |

In addition to the enediyne biosynthetic loci found in the above organisms not previously reported to produce an enediyne natural product, the genome scanning method was used to identify enediyne biosynthetic loci from the *Streptomyces cavourensis* subsp. *washingtonensis* NRRL B-8030, *Streptomyces kaniharaensis* ATCC 21070, *Streptomyces citricolor* IFO 13005, as well as from 3 new actinomycete strains isolated from soil samples. Enediyne biosynthetic loci were identified by the presence of the conserved enediyne warhead cassette genes as well as other genes frequently found in biosynthetic loci encoding other natural product classes. These additional examples are disclosed in co-pending U.S. Ser. No. 10/152,886 or in a manuscript submitted for publication, or both. In addition, the neocarzinostatin locus was cloned from *Streptomyces carzinostaticus* subsp. *neocarzinostaticus* ATCC 15944 using the genome scanning method, and was confirmed to direct neocarzinostatin biosynthesis by gene inactivation and complementation experiments (W. Liu et al., Biosynthesis of the enediyne antitumor antibiotic C-1027, *Science*, 297 (5584): 1170–3.

Example 2

Use of Genome Scanning to Identify Glycosylated Lipopeptide Clusters and Acidic Lipopeptide Clusters in Known Lipopetide Producing Organisms and in Organisms not Previously Reported to Produce Lipopeptide Natural Products

*Actinoplanes* sp. ATCC 33076 was known to produce ramoplanin, a biologically active lipodepsipeptide (U.S. Pat. No. 4,303,646). The genetic locus involved in the production of this compound was not previously identified.

*Actinoplanes* sp. strain ATCC 33076 was obtained from the American Tissue Culture Collection (ATCC) and cultured according to standard microbiological techniques (Kieser et al., *Practical Streptomyces Genetics*, John Innes Center, Norwich Research Park, Colney, Norwich NR4 6UH England, 2000). Confluent mycelia from oatmeal agar plates were used for the extraction of genomic DNA as previously described (Kieser et al., supra) and the size range of the DNA obtained was assessed on agarose gels by electrical field inversion techniques as described by the manufacturer (FIGE, BioRad).

To prepare a small insert library, genomic DNA was randomly sheared by sonication. DNA fragments having a size range between 1.5 and 3 kb were fractionated on a agarose gel and isolated using standard molecular biology techniques (Sambrook et al., supra). The ends of the obtained DNA fragments were repaired using T4 DNA polymerase (Roche) as described by the supplier. The repaired DNA fragments were subcloned into a derivative of pBluescript SK+ vector (Stratagene) which does not allow transcription of cloned DNA fragments. The vector was selected as it contains a convenient polylinker region surrounded by sequences corresponding to universal sequencing primers such as T3, T7, SK, and KS (Stratagene). The EcoRV restriction site found in the polylinker region was used as it allows insertion of blunt-end DNA fragments. Ligation of the inserts, use of the ligation products to transform *E. coli* DH10B host and selection for recombinant clones were performed according o conventional techniques (Sambrook et al., supra). Plasmid DNA carrying the *Actinoplanes* sp. genomic DNA fragments was extracted and the insert size of 1.5 to 3 kb was confirmed by electrophoresis on agarose gels.

The genomic DNA was also used to generate a large insert library. High molecular weight genomic DNA was partially digested with a frequent cutting restriction enzyme, Sau3A (G|ATC). This enzyme generates random fragments of DNA ranging from the initial undigested size of the DNA to short fragments of which the length is dependent upon the frequency of the enzyme DNA recognition site in the genome and the extent of the DNA digestion. Conditions generating DNA fragments having an average length of about 40 kb were chosen (Sambrook et al., supra). The Sau3A restricted DNA was ligated into the BamHI site of the SuperCos-1 cosmid cloning vector (Stratagene) and packaged into phage particles (Gigapack III XL, Stratagene) as specified by the supplier. *E. coli* strain DH10B was used as host and 864 recombinant clones carrying cosmids were selected and propagated to generate the large-insert library. Considering an average size of 8 Mb for a streptomyces genome and an average size of 35 kb of genomic insert in the large insert library, this library represents about a 4-fold coverage of the microorganism's entire genome. The *Actinoplanes* sp. large-insert library was transferred onto membrane filters (Schleicher & Schnell) as specified by the manufacturer.

The short-insert and large insert libraries were analyzed by sequence determination of the cloned genomic DNA inserts. The universal primers KS or T7, referred to as forward (F) primer, were used to initiate polymerization of labeled DNA. Extension of at least 700 bp from the priming site can be routinely achieved using the TF, BDT v2.0 sequencing kit as specified by the supplier (Applied Biosystems). Sequence analysis of the fragments generated, i.e. the GSTs, was performed using a 3700 ABI capillary electrophoresis DNA sequencer (Applied Biosystems). The average length of the DNA sequence reads forming a GST was about 700 bp. Further analysis of the obtained GSTs was performed by sequence homology comparison to various protein sequence databases. The DNA sequences of the obtained GSTs were translated into amino acid sequences and compared to the National Center for Biotechnology Information (NCBI) nonredundant protein database and the DECIPHER™ database (Ecopia BioSciences, St-Laurent, Quebec, CANADA) using the the BLASTP algorithm with the default parameters (Altschul, S. F. et al. Gapped BLAST nd PSI-BLAST: a new generation of protein database search programs, *Nucleic Acids Res.*, 25, 3389–3402 1997). Sequence similarity with known proteins of defined function in the database enables one to make predictions on the function of the partial protein that is encoded by the translated GST.

882 *Actinoplanes* sp. GSTs were generated from the small insert library and 48 GSTs were generated from the large insert library for a total of 930 GSTs and analyzed by sequence comparison. Sequence alignments displaying an E value of at least e-5 were considered as significantly homologous and retained for further evaluation. GSTs showing similarity to a gene of interest were selected and used to identify larger segments of genomic DNA including the gene of interest. Ramoplanins produced by *Actinoplanes* sp. belong to the family of polypeptide antibiotics. Polypeptides are synthesized by nonribosomal peptide synthetase (NRPS) enzymes that perform a series of condensations and modifications of aminoacids. Many members of this enzymatic class are found in protein databases rendering possible the identification of an unknown NRPS by sequence similarity. Analysis of the *Actinoplanes* sp. GSTs revealed the presence of 3 GSTs having similarity to known NRPS proteins in the NCBI nonredundant protein database (Table 9). The obtained E values confirm that these GSTs encode partial NRPS sequences. The 3 NRPS GSTs were selected for the generation of oligonucleotide probes which were then used to identify gene clusters harboring the specific NRPS genes in the large insert library.

Oligonucleotide probes were designed from the nucleotide sequence of the selected GSTs, radioactively labeled, and hybridized to the large- insert library using standard molecular biology techniques (Sambrook et al., supra, Schleicher & Schnell). Positive clones were identified, cosmid DNA was extracted (Sambrook et al., supra) and entirely sequenced using a shotgun sequencing approach (Fleischmann et al., *Science*, 269:496–512). Identification of the original GSTs, used to generate the oligonucleotide probes, within the DNA sequence of the obtained cosmids proved that these cosmids indeed carried the gene cluster of interest.

Generated sequences were assembled using the Phred-Phrap algorithm (University of Washington, Seattle, USA) recreating the entire DNA sequence of the cosmid insert. Reiterations of hybridizations of the large insert library with probes derived from the ends of the original cosmid allow indefinite extension of sequence information on both sides of the original cosmid sequence until the complete target gene cluster is obtained. Application of this method on *Actinoplanes* sp. and use of the above-described NRPS GST probes yielded 6 cosmids. Complete sequence of these cosmids and analysis of the proteins encoded by them undoubtedly demonstrated that the gene cluster obtained was indeed responsible for the production of ramoplanin. Subsequent inspection of the ramoplanin biosynthetic cluster sequence (~88 kb) revealed the presence of 3 additional GSTs from the large insert library, bringing the total number of ramoplanin locus GSTs to 6. The genetic locus responsible for the biosynthesis of ramoplanin and identified according to the present invention is disclosed in U.S. Ser. No. 09/976,059 filed on Oct. 15, 2001.

TABLE 9

| | Length (bp) | Proposed function | Homology | Probability | Proposed function of protein match |
|---|---|---|---|---|---|
| GST1 | 632 | NRPS | PIR T36248 | $3.00^E-20$ | CDA peptide synthetase I in *Streptomyces coelicolor* |
| GST2 | 592 | NRPS | PIR T36248 | $5.00^E-28$ | CDA peptide synthetase I in *Streptomyces coelicolor* |
| GST3 | 502 | NRPS | PIR T36180 | $7.00^E-31$ | CDA peptide synthetase III in *Streptomyces coelicolor* |

The genome scanning method of the present invention was used to discover an acidic lipopeptide biosynthetic locus in *Streptomyces refuineus* subsp. *thermotolerans* NRRL 3143 which was not previously reported to produce a lipepetpide natural product.

*Streptomyces refuineus* subsp. *thermotolerans* NRRL 3143 was obtained from the Agricultural Research Service collection (National Center for Agricultural Utilization Research, 1815 N. University Street, Peoria, Ill. 61604) and cultured using standard microbiological techniques. The organism was propagated on oatmeal agar medium at 28 degrees Celsius for several days. For isolation of high molecular weight genomic DNA, cell mass from three freshly grown, near confluent 100 mm petri dishes was used. The cell mass was collected by gentle scraping with a plastic spatula. Residual agar medium was removed by repeated washes with STE buffer (75 mM NaCl; 20 mM Tris-HCl, pH 8.0; 25 mM EDTA). High molecular weight DNA was isolated by established protocols (Kieser et al. supra) and its integrity was verified by field inversion gel electrophoresis (FIGE) using the preset program number 6 of the FIGE MAPPER™ power supply (BIORAD). This high molecular weight genomic DNA serves for the preparation of a small insert library and a large insert library. Both libraries contained randomly generated *Streptomyces refuineus* genomic DNA fragments.

For the generation of the small insert library, genomic DNA was randomly sheared by sonication. DNA fragments having a size range between 1.5 and 3 kb were fractionated on a agarose gel and isolated using standard molecular biology techniques (Sambrook et al., supra). The ends of the obtained DNA fragments were repaired using T4 DNA polymerase (Roche) as described by the supplier. This enzyme creates DNA fragments with blunt ends that can be subsequently cloned into an appropriate vector. The repaired DNA fragments were subcloned into a derivative of pBluescript SK+ vector (Stratagene) which does not allow transcription of cloned DNA fragments. This vector was selected as it contains a convenient polylinker region surrounded by sequences corresponding to universal sequencing primers such as T3, T7, SK, and KS (Stratagene). The unique EcoRV restriction site found in the polylinker region was used as it allows insertion of blunt-end DNA fragments. Ligation of the inserts, use of the ligation products to transform *E. coli* DH10B (Invitrogen) host and selection for recombinant clones were performed as previously described (Sambrook et al., supra). Plasmid DNA carrying the *Streptomyces refuineus* genomic DNA fragments was extracted by the alkaline lysis method (Sambrook et al., supra) and the insert size of 1.5 to 3 kb was confirmed by electrophoresis on agarose gels.

The large insert library was constructed from the *Streptomyces refuineus* high molecular weight gehomic DNA using the SuperCos-1 cosmid vector (Stratagene™). The cosmid arms were prepared as specified by the manufacturer. The high molecular weight DNA was subjected to partial digestion at 37 degrees Celsius with approximately one unit of Sau3AI restriction enzyme (New England Biolabs) per 100 micrograms of DNA in the buffer supplied by the manufacturer. This enzyme generates random fragments of DNA ranging from the initial undigested size of the DNA to short fragments of which the length is dependent upon the frequency of the enzyme DNA recognition site in the genome and the extent of the DNA digestion. At various timepoints, aliquots of the digestion were transferred to new microfuge tubes and the enzyme was inactivated by adding a final concentration of 10 mM EDTA and 0.1% SDS. Aliquots judged by FIGE analysis to contain a significant fraction of DNA in the desired size range (30–50 kb) were pooled, extracted with phenol/chloroform (1:1 vol:vol), and pelletted by ethanol precipitation. The 5' ends of Sau3AI DNA fragments were dephosphorylated using alkaline phosphatase (Roche) according to the manufacturer's specifications at 37 degrees Celcius for 30 min. The phosphatase was heat inactivated at 70 degrees Celcius for 10 min and the DNA was extracted with phenol/chloroform (1:1 vol:vol), pelletted by ethanol precipitation, and resuspended in sterile water. The dephosphorylated Sau3AI DNA fragments were then ligated overnight at room temperature to the SuperCos-1 cosmid arms in a reaction containing approximately four-fold molar excess SuperCos-1 cosmid arms. The ligation products were packaged using Gigapack® III XL packaging extracts (Stratagene™) according to the manufacturer's specifications. From the large insert library 864 isolated cosmid clones in *E. coli* DH10B (Invitrogen) were generated.

The large insert library clones were picked and inoculated into nine 96-well microtiter plates containing LB broth (per liter of water: 10.0 g NaCl; 10.0 g tryptone; 5.0 g yeast extract) which were grown overnight and then adjusted to contain a final concentration of 25% glycerol. These microtiter plates were stored at –80 degrees Celcius and served as glycerol stocks of the large insert library. Duplicate microtiter plates were arrayed onto nylon membranes as follows. Cultures grown on microtiter plates were concentrated by pelleting and resuspending in a small volume of LB broth. A 3×3 96-pin grid was spotted onto nylon membranes. These membranes representing the large insert library were then layered onto LB agar and incubated overnight at 37 degrees Celcius to allow the colonies to grow. The membranes were layered onto filter paper pre-soaked with 0.5 N NaOH/1.5 M NaCl for 10 min to denature the DNA and then neutralized by transferring onto filter paper pre-soaked with 0.5 M Tris (pH 8)/1.5 M NaCl for 10 min. Cell debris was gently scraped off with a plastic spatula and the DNA was crosslinked onto the membranes by UV irradiation using a GS GENE LINKER™ UV Chamber (BIORAD). Considering an average size of 8 Mb for an actinomycete genome and an average size of 35 kb of genomic insert in the large insert library, the 864 cosmid clones from the library represents roughly a 4-fold coverage of the microorganism's entire genome.

The small insert and large insert libraries were analyzed by sequence determination of the cloned genomic DNA inserts. The universal primers KS or T7, referred to as forward (F) primers, were used to initiate polymerization of labeled DNA. Extension of at least 700 bp from the priming site can be routinely achieved using the TF, BDT v2.0 sequencing kit as specified by the supplier (Applied Biosystems). Sequence analysis of the small genomic DNA fragments to generate a database of GSTs was performed using a 3700 ABI capillary electrophoresis DNA sequencer (Applied Biosystems). The average length of the DNA sequence reads was ~700 bp. Further analysis of the obtained GSTs was performed by sequence homology comparison to various protein sequence databases. The DNA sequences of the obtained GSTs were translated into amino acid sequences and compared to the National Center for Biotechnology Information (NCBI) nonredundant protein database and the DECIPHER™ database (Ecopia BioSciences, Inc., St. Laurent, Quebec, CANADA) using the BLASTP algorithm with the default parameters (Altschul et al., supra).

486 *Streptomyces refuineus* GSTs were generated from the small insert library and 185 GSTs were generated from the large insert library for a total of 671 GSTs and analyzed by sequence comparison using the BLASTP algorithm. Sequence alignments displaying an E value of at least e-5 were considered as significantly homologous and retained for further evaluation. GSTs showing similarity to a gene of interest can be at this point selected and used to identify larger segments of genomic DNA from the large insert library that include the gene(s) of interest. Polypeptide natural products are often synthesized by nonribosomal peptide synthetase (NRPS) enzymes that perform a series of condensations and modifications of amino acids. Many members of this enzymatic class are found in protein databases rendering possible the identification of an unknown NRPS by sequence similarity. Analysis of the *Streptomyces refuineus* GSTs by Blast analysis revealed the presence of at least one GST from the small insert library having similarity to known NRPS proteins in the NCBI nonredundant protein database (GST1, Table 10). Closer inspection of the NRPS sequence obtained from the forward read revealed that it contained the C-terminal portion of an NRPS condensation (C) domain followed by the N-terminal portion of an NRPS adenylation (A) domain, both of which were in the same reading frame and were in the same orientation relative to the forward primer. Sequencing of this GST clone with the reverse primer followed by Blast analysis also revealed similarity to known NRPS proteins in the NCBI nonredundant protein database (GST1 Reverse, Table 10). Closer inspection of the NRPS sequence obtained from the reverse read revealed that it contained an internal portion of an NRPS condensation (C) domain that includes the proposed active-site motif (HHXXXDG: SEQ ID NO: 1) of condensation domains (Stacheihaus et al. J. Biol. Chem. 1998 Vol. 273 pp. 22773–2278 1). As expected, the orientation of this C domain sequence is opposite to that of the reverse primer. Thus this GST clone harbours an insert that is a portion of an NAPS gene. The sequence obtained with the reverse primer was selected for the generation of an oligonucleotide probe which was then used to identify the gene cluster harboring this specific NAPS gene(s) in the large insert library. National Center for Biotechnology Information (NCBI) nonredundant protein database DECIPHER™ database (Ecopia BioSciences, St. Laurent, Quebec CANADA) using the BLASTP algorithm with the default parameters (Altschul et al., supra).

486 *Streptomyces refuineus* GSTs were generated from the small insert library and 185 GSTs were generated from the large insert library for a total of 671 GSTs and analyzed by sequence comparison using the BLASTP algorithm. Sequence alignments displaying an E value of at least e-5 were considered as significantly homologous and retained for further evaluation. GSTs showing similarity to a gene of interest can be at this point selected and used to identify larger segments of genomic DNA from the large insert library that include the gene(s) of interest. Polypeptide natural products are often synthesized by nonribosomal peptide synthetase (NRPS) enzymes that perform a series of condensations and modifications of amino acids. Many members of this enzymatic class are found in protein databases rendering possible the identification of an unknown NRPS by sequence similarity. Analysis of the *Streptomyces refuineus* GSTs by Blast analysis revealed the presence of at least one GST from the small insert library having similarity to known NRPS proteins in the NCBI nonredundant protein database (GST1, Table 10). Closer inspection of the NRPS sequence obtained from the forward read revealed that it contained the C-terminal portion of an NRPS condensation (C) domain followed by the N-terminal portion of an NRPS adenylation (A) domain, both of which were in the same reading frame and were in the same orientation relative to the forward primer. Sequencing of this GST clone with the reverse primer followed by Blast analysis also revealed similarity to known NRPS proteins in the NCBI nonredundant protein database (GST1 Reverse, Table 10). Closer inspection of the NRPS sequence obtained from the reverse read revealed that it contained an internal portion of an NRPS condensation (C) domain that includes the proposed active-site motif (HHXXXDG) of condensation domains (Stachelhaus et al. J. Biol. Chem. 1998 Vol. 273 pp. 22773–22781). As expected, the orientation of this C domain sequence is opposite to that of the reverse primer. Thus this GST clone harbours an insert that is a portion of an NRPS gene. The sequence obtained with the reverse primer was selected for the generation of an oligonucleotide probe which was then used to identify the gene cluster harboring this specific NRPS gene(s) in the large insert library.

Hybridization oligonucleotide probes were radiolabeled with $P^{32}$ using T4 polynucleotide kinase (New England Biolabs) in 15 microliter reactions containing 5 picomoles of oligonucleotide and 6.6 picomoles of [$\gamma$-$P^{32}$]ATP in the kinase reaction buffer supplied by the manufacturer. After 1 hour at 37 degrees Celcius, the kinase reaction was terminated by the addition of EDTA to a final concentration of 5 mM. The specific activity of the radiolabeled oligonucleotide probes was estimated using a Model 3 Geiger counter (Ludlum Measurements Inc., Sweetwater, Tex.) with a built-in integrator feature. The radiolabeled oligonucleotide probes were heat-denatured by incubation at 85 degrees Celcius for 10 minutes and quick-cooled in an ice bath immediately prior to use.

TABLE 10

| | Length (bp) | Proposed function | BLAST Homology | Probability | Proposed function of protein match |
|---|---|---|---|---|---|
| GST1 | 581 | NRPS (C + A domains) | PIR T36248 | $9.00^{E}-26$ | CDA peptide synthetase I of *Streptomycos coelicolor* |
| GST1 Reverse | 410 | NRPS (C domain) | PIR T36249 | $9.00^{E}-30$ | CDA peptide synthetase II of *Streptomyces coelicolor* |

The large insert library membranes were pretreated by incubation for at least 2 hours at 42 degrees Celcius in Prehyb Solution (6×SSC; 20 mM $NaH_2PO_4$; 5× Denhardt's; 0.4% SDS; 0.1 mg/ml sonicated, denatured salmon sperm DNA) using a hybridization oven with gentle rotation. The membranes were then placed in Hyb Solution (6×SSC; 20 mM $NaH_2PO_4$; 0.4% SDS; 0.1 mg/ml sonicated, denatured salmon sperm DNA) containing $1\times10^6$ cpm/ml of radiolabeled oligonucleotide probe and incubated overnight at 42 degrees Celcius using a hybridization oven with gentle rotation. The next day, the membranes were washed with Wash Buffer (6×SSC, 0.1% SDS) for 45 minutes each at 46, 48, and 50 degrees Celcius using a hybridization oven with gentle rotation. The membranes were then exposed to X-ray film to visualize and identify the positive cosmid clones. Positive clones were identified, cosmid DNA was extracted from 30 ml cultures using the alkaline lysis method (Sambrook et al., supra) and the inserts were entirely sequenced using a shotgun sequencing approach (Fleischmann et al., Science, 269:496–512).

Sequencing reads were assembled using the Phred-Phrap™ algorithm (University of Washington, Seattle, USA) recreating the entire DNA sequence of the cosmid insert. Reiterations of hybridizations of the large insert library with probes derived from the ends of the original cosmid allow indefinite extension of sequence information on both sides of the original cosmid sequence until the complete sought-after gene cluster is obtained. Overlapping cosmid clones that were detected by the oligonucleotide probe derived from the GST1 clone have been completely sequenced and disclosed in co-pending U.S. S. No. 60/372,789. Subsequent inspection of the biosynthetic cluster sequence (~53 kb) with the database of GST sequences generated from the *Streptomyces refuineus* small insert library revealed that a total of 5 GSTs were contained within this cluster. Protein sequence homology was evaluated with proteins found in the GenBank database of protein sequences (National Center for Biotechnology Information, National Library of Medicine, Bethesda, Md., USA) using the BLASTP algorithm (see e.g. Altshul et al. 1997 *Nucleic Acids Res.*, vol. 25, pp. 3389–3402) and the results of this homology search are disclosed in U.S. S. No. 60/372,789. Thus, *Streptomyces refuineus* subsp. *thermotolerans* NRRL 3143 which was not previously reported to produce a lipopeptide natural product was found to contain an acidic lipopeptide biosynthetic locus.

Example 3

Use of Genome Scanning to Identify a Macrolide Natural Product From an Organism not Previously Reported to Produce a Macrolide Natural Product

*Micromonospora carbonacea* was known to produce the antimicrobial orthosomycin natural product everninomicin. *icromonospora carbonacea* was not previously reported to produce other natural products. Using the procedures described in regard to *Streptomyces macromyceticus* (Example 1) and *Streptomyces refuineus* (Example 2), we have surprisingly discovered in the *Micromonospora carbonacea* genome, a type I polyketide biosynthetic gene cluster directed to the production of a rosaramicin-type polyketide. Rosaramicin is a 16-member macrolide.

*Micromonospora carbonacea* var. *aurantiaca* NRRL 2997 was obtained from the Agricultural Research Service collection (National Center for Agricultural Utilization Research, 1815 N. University Street, Peoria, Ill. 61604) and cultured using standard microbiological techniques. The organism was propagated on oatmeal agar medium at 28 degrees Celsius for several days and cell mass from three freshly grown, near confluent 100 mm petri dishes was collected. Residual agar medium was removed by repeated washes with STE buffer (75 mM NaCl; 20 mM Tris-HCl, pH 8.0; 25 mM EDTA). High molecular weight DNA was isolated by established protocols and its integrity was verified by field inversion gel electrophoresis (FIGE) using the preset program number 6 of the FIGE MAPPER™ power supply (BIORAD). The high molecular weight genomic DNA served for the preparation of a small insert library and a large insert library.

The small insert and large insert libraries were analyzed by sequence determination of the cloned genomic DNA inserts. The universal primers KS or T7, referred to as forward (F) primers, were used to initiate polymerization of labeled DNA. Extension of at least 700 bp from the priming site can be routinely achieved using the TF, BDT v2.0 sequencing kit as specified by the supplier (Applied Biosystems). Sequence analysis of the small genomic DNA fragments was performed using a 3700 ABI capillary electrophoresis DNA sequencer (Applied Biosystems) to generate GSTs. The average length of the DNA sequence reads was about 700 bp. The DNA sequences of the GSTs were translated into amino acid sequences and compared to the National Center for Biotechnology Information (NCBI) nonredundant protein database and the DECIPHER™ database using that BLASTP algorithms with the default parameters (Altschul et al., supra).

437 *M. carbonacea* GSTs were generated using the forward sequencing primer and an additional 71 GSTs were generated from the large insert library, for a total of 508 GSTs, the GSTs were analyzed by sequence comparison using the BLASTP algorithm. GSTs showing similarity to a gene of interest were used to identify larger segments of genomic DNA from the large insert library. Polyketide natural products are often synthesized by type I polyketide synthases (PKSs). Several forward GST reads from the small insert library were identified as portions of PKS genes. For example, one such GST encoded an internal portion of a PKS acyl transferase (AT) domain in the antisense orientation relative to the sequencing primer. The large insert library clone from which this GST was obtained was also sequenced using the reverse sequencing primer and was found to encode the N-terminal portion of a PKS ketosynthase (KS) domain in the sense orientation relative to the sequencing primer. Based on the sequence of the forward read of the large insert library clone, a radiolabeled oligonucleotide probe was designed to identify and isolate large insert library clones which harbored the sequences of interest. Reiterations of hybridizations of the large insert library with probes derived from the ends of the original cosmid allowed for extension of sequence information on both sides of the original cosmid sequence until the complete gene cluster was obtained.

Three overlapping cosmid clones that were either directly identified by the original oligonucleotide probe (derived from the short insert library clone) or by probes derived from the ends of the original cosmids have been completely sequenced to provide over 60 Kb of genetic information. Subsequently, the forward and reverse reads of the short insert library clone from which the original oligonucleotide probe was derived were mapped to a region of the rosaramicin biosynthetic locus that encodes a portion of the PKS gene. The PKS gene corresponded to a small insert library clone with an insert size of approximately 2.6 kb, in good agreement with the selected size range of 1.5–3 kb.

To confirm that the gene cluster obtained was indeed responsible for the production of a glycosylated macrolide consistent with the structure of rosaramicin, *M. carbonacea* var *aurantiaca* NRRL 2997 was cultured and the fermentation broth analysed. *Micromonospora carbonacea aurantiaca* NRRL 2997 was cultured on a 30 ml media A plate (glucose 1.0%, dextrin 4.0%. sucrose 1.5%, casein enzymatic hydrolysate 1.0%, $MgSO_4$ 0.1%, $CaCO_3$ 0.2%, and agar 2.2 g/100 ml) at 30° C. for 14 days. The cells and agar were added to 25 ml of 95% ethanol and incubated at room temperature for 2 h under agitation. The ethanol phase was collected and the extraction step was repeated under the same conditions. The ethanol was evaporated from the pooled extracts and the residue was freeze-dried. The residue was then resuspended in 1.0 ml of water.

The C-18 solid phase column (Burdick & Jackson) was conditioned before use by sequential washing with 3 ml of distilled water, 3 ml of methanol, and finally 3 ml of distilled water. The residue previously resuspended in 1.0 ml of water was loaded on the conditioned solid phase extraction system (SPE). Following passage of the sample though the SPE column washes were performed first, with 5 ml of water to remove polar materials, and then with 70% acetone and 30% methanol to elute a secondary metabolite-containing fraction which was then freeze-dried. This organic fraction was dissolved in 300 ul of 50% acetonitrile-distilled water.

Chemical analysis of the organic fraction from the SPE column was performed by HPLC-ES-MS (Waters, ZQ systems). The extracts (50.0 ul) were separated on a C18 symmetry analytical column (2.1×150 mm) with HPLC 2690 system (Waters) using a 60-min linear gradient from 30% acetonitrile-5 mM ammonium acetate to 95% acetonitrile-5 mM ammonium acetate at a flow rate of 150 ul min$^{-1}$. UV and visible light absorption spectra (220 to 500 nm) were acquired with a PDA (Waters) by using the column effluents prior to their analysis by ES-MS. The electrospray source was switched between positive ion mode and negative ion mode at 0.3 s intervals to acquire both positive and negative ion spectra. The cone voltage was 25.0 V. The capillary was maintained at 3.0 V. The source temperature was kept at 100° C. The desolvation temperature was kept at 400° C. and the desolvation gas flow was 479 liter.h$^{-1}$. The data collection and analysis were performed with Mass-Lynx V3.5 program (Waters). A UV spectra at a retention time of 24.4 minutes and a MS spectra showing a molecular ion consistent with rosaramicin at retention time 24.4 minutes (mass of 582.57 [M+H]$^+$) were obtained.

The full biosynthetic locus for rosaramicin from *Micromonospora carbonacea aurantiaca* and the UV spectra obtained by HPLC-MS are disclosed in co-pending application U.S. Ser. No. 10/205,032.

Example 4

Use of Genome Scanning to Identify Orthosomycin Natural Products and to Distinguish Between Everninomicin-type Orthosomycins and Avilamycin-type Orthosomycin From an Organism Known to Produce an Orthosomycin and From an Organism not Previously Reported to Produce an Orthosomycin Everninomicins are oligosaccharide antibiotics that are members of the orthosomycin chemical class. This class is characterized by the presence of orthoester groups joining, together with glycosidic linkages, various deoxysugar residues. Everninomicins are produced by several variants of the microorganism *Micromonospora carbonacea* (Weinstein et al., *Antimicrobial Agents and Chemotherapy*—1964, 24–32,1964; U.S. Pat. No. 3,499,078). Distinguishing features everninomicin-type orthosomycins and avilamycin-type orthosomycin are reviewed in co-pending application U.S. Ser. No. 10/107,431.

Genome scanning procedures described above were used to identify the everninomycin biosynthetic locus from *Micromonospora carbonacea subsp. aurantiaca* strain NRRL 2997 obtained from the Agricultural Research Service collection (ARS). The presence of several deoxysugar residues in the chemical structure everninomicins is a clear indication that well-described enzymatic activities involved in the generation of these unusual sugar residues should participate in the biosynthesis of these compounds. Analysis of 437 GSTs derived from the short insert library and the large insert library of genomic DNA from *M. carbonacea* revealed the presence of two GSTs having sequence homology to enzymes involved in the synthesis of deoxysugar residues from natural sugar precursors (Table 11).

TABLE 11

|  | Length (bp) | Proposed function | Homology | Probability | Proposed function of protein match |
|---|---|---|---|---|---|
| GST1 | 787 | sugar dehydratase | PIR T30873 | $6.00^E$–90 | dNDP-glucose dehydratase in *Streptomyces viridochromogenes* |
| GST2 | 601 | dNTP-sugar synthase | PIR T30872 | $9.00^E$–38 | dNDP-glucose synthase in *Streptomyces viridochromogenes* |

Both GSTs were used as probes for screening the *Micromonospora carbonacea* large insert library. Overlapping cosmids positive for both probes were obtained suggesting a near proximity for the two GSTs in the gene cluster. Analysis of sequenced cosmids revealed the presence of the original GSTs confirming that the obtained gene cluster was indeed the targeted one. After two reiterations of this method, 3 overlapping cosmids were obtained.

DNA sequence determination of these cosmids and analysis of the encoded proteins by sequence similarity undoubtedly established this locus as the one responsible for the biosynthesis of everninomicin. Additional DNA sequence inspection of the everninomicin locus (~58 kb) showed that a total of 7 GSTs obtained from the original screening of the short insert library, including the ones that were used to probe the large insert library, were part of the everninomicin locus. The genetic locus responsible for the biosynthesis of everninomicin, identified according to the present invention, is disclosed in U.S. Ser. No. 09/769,734 filed on Jan. 27, 2001.

*Streptomyces mobaraensis* was previously shown to naturally produce a variety of biologically active compounds including piericidins, pactamycin, and detoxins (Tamura et al., 1963, Agr. Biol. Chem., Vol. 27, No. 8, pp. 576–582). *Streptomyces mobaraensis* was not previously reported to produce an orthosomycin.

*Streptomyces mobaraensis* strain NRRL B-3729 was obtained from the Agricultural Research Service collection (ARS) and cultured according to standard microbiological techniques. Genome scanning procedures as described in regards to *Streptomyces macromyceticus* (Example 1) and *Streptomyces refuineus* (Example 2) were used to identify a genetic locus responsible for the production of an avilamycin-like compound. A total of 450 GSTs were generated and analyzed by sequence comparison. Among these GSTs, two showed similarity to enzymes involved in deoxysugar biosynthesis (Table 12).

TABLE 12

| | Length (bp) | Proposed function | Homology | Probability | Proposed function of protein match |
|---|---|---|---|---|---|
| GST1 | 738 | sugar dehydratase | PIR T30873 | $2.00^{E}-74$ | dNDP-glucose dehydratase in *Streptomyces viridochromogenes* |
| GST2 | 601 | glycosyltransferase | PIR F75099 | 2.00E-05 | rhamnosyl transferase in *Pyrococcus abyssii* |

There are several classes of natural compounds such as macrolides, polypeptides, anthracyclines, enediynes, polyenes that are glycosylated with typical and/or unusual glycosyl groups. Other metabolites such as orthosomycins and aminoglycosides are mainly composed of modified deoxysugar moieties (Weymouth-Wilson, The role of carbohydrates in biologically active natural products, *Nat. Prod. Rep.*, 1997, 99–110). Specific enzymes are required for the biosynthesis of unusual sugars from natural sugar precursors as well as glycosyltransferase enzymes that catalyze the transfer of the sugar to a specific backbone structure (Liu and Thorson, Pathways and mechanisms in the biogenesis of novel deoxysugars by bacteria, *Annu. Rev. Microbiol.*, 48: 223–256). The presence of two sugar biosynthetic genes in *Streptomyces mobaraensis* was of interest as the natural products shown to be produced by this microorganism do not contain any sugar residue.

GST1 was used to probe the *S. mobaraensis* large insert library. Positive clones were identified and sequenced. The original GST1 was identified within the sequenced cosmid. One reiteration of the same method was applied providing two overlapping cosmids covering the entire biosynthetic cluster. Analysis of the proteins encoded by this cluster demonstrated the presence of a novel biosynthetic locus (~45 kb) having the potential to produce an avilamycin-like compound, member of the orthosomycin group of antibiotics composed of a series of deoxysugar residues. The genetic locus responsible for the biosynthesis of this avilamycin-like compound and identified according to the present invention is disclosed in U.S. Ser. No. 10/107,431 filed on Mar. 28, 2002.

Example 5

Use of Genome Scanning to Identification an Anthramycin Biosynthetic Locus in *Streptomyces refuineus*.

*Streptomyces refuineus* var. *thermotolerans* was shown to produce a benzodiazepine antibiotic, anthramycin, that covalently binds to the minor groove of DNA. Anthramycin has been shown to possess various potent biological activities including antibiotic, antitumor and antiviral activities. The biosynthetic locus responsible for the production of anthramycin was not previously characterized.

*Streptomyces refuineus* var. *thermotolerans* strain NRRL-3143 was obtained from the Agricultural Research Service collection (ARS) and cultured using standard microbiological techniques (Kieser et al., supra). Subsequent experimental procedures for cloning and analyzing the genetic material of this microorganism were as described in regards to *Streptomyces macromyceticus* (Example 1) and *Streptomyces refuineus* (Example 2).

A total of 671 GSTs were analyzed by sequencing and protein homology comparison to the NCBI protein database and the DECIPHER™ database. Precursor feeding studies have established two distinct moieties in the anthramycin molecule that derive from tryptophan via the kynurenine pathway and catabolism of L-tyrosine (Hurley et al., 1975). The two modified amino acids are linked together through an amide bond typically catalyzed by nonribosomal peptide synthetases (NRPS). Analysis of the *S.refuineus* GSTs derived from the small insert library revealed the presence of a GST showing amino acid similarity to an alpha-aminoadipate reductase protein in *Candida albicans*, enzyme that has a domain organization similar to those of NRPSs (Table 13).

TABLE 13

| | Length (bp) | Proposed function | Homology | Probability | Proposed function of protein match |
|---|---|---|---|---|---|
| GST1 | 426 | reductase | gb AAC02241.1 | 2.00E-06 | alpha-aminoadipate reductase in *Candida albicans* |

This GST was subsequently used to probe the *S. refuineus* large insert library. Cosmids positive by hybridization were obtained and analyzed by sequence determination. The presence of the original GST that was used to screen the large insert library was determined in the sequenced cosmid confirming that this cosmid carried the sought-after gene cluster. After one reiteration of the described method, two overlapping cosmids covering the entire anthramycin biosynthetic locus were obtained. Analysis of the genetic information derived from these two cosmids clearly demonstrated the presence and defined the boundaries of the anthramycin biosynthetic locus (~33 kb). The genetic locus responsible for the biosynthesis of anthramycin and identified according to the present invention is disclosed in co-pending application U.S. Ser. No. 10/166,087 filed Jun. 11, 2002.

Example 6

Use of Genome Scanning to Identify a Gene Cluster Characterized by an Polyketide Synthase Having an Unusual Domain Organization Dorrigocins and migrastatins are polyketides. Type I polyketide synthase (PKS) enzymes are responsible for producing a large number of 12-, 14- and 16-membered macrolide antibiotics. Type I PKS polypeptides contain multiple domains and the order of catalytic domains has been conserved in all type I PKSs reported to date. Thus, when all beta-keto processing domains are present in a module, the order of domains in that module from N-to-C-terminus has always been found to be KS, AT, DH, ER, KR, and ACP. Some or all of the beta-keto processing domains may be missing in particular modules, but the order of the domains present in a module has remained the same in all reported cases. The method of the invention was used find the gene cluster responsible for producing dorrigocin and migrastatin, discovery of which by other methods had been frustrated by an unusual domain organization wherein the polyketide synthase does not contain an AT domain attached to a PKS domain, but rather wherein the AT function is provided in trans by a distinct component. This unusual organization is described in more detail in co-pending application U.S. Ser. No. 10/132,134.

Streptomyces platensis subsp. rosaceusstrain AB1981F-75 (NRRL 18993) was obtained from the Agricultural Research Service collection (National Center for Agricultural Utilization Research, 1815 N. University Street, Peoria, Ill. 61604) and cultured using standard microbiological techniques. Subsequent experimental procedures for cloning and analyzing the genetic material of this microorganism were as described in regards to Streptomyces macromyceticus (Example 1) and Streptomyces refuineus (Example 2).

A total of 1536 S. platensis GSTs were generated and analyzed by sequence comparison using the BLASTP algorithm with the default parameters (Altschul et al., supra). As dorrigocins and migrastatin are polyketides, several S. platensis GSTs that were clearly portions of type I PKS genes were pursued. Using these type I PKS GSTs, we indeed identified a type I PKS locus in S. platensis, however, the PKS domain order and number of modules of this type I PKS was inconsistent with the structures of dorrigocins and migrastatin. In addition to the GSTs that were clearly portions of type I PKS genes, we also identified GSTs that were somewhat related to type I PKS genes. When the latter were used as probes to screen the CIL library and the resulting cosmid clones were sequenced, an unusual PKS gene cluster was identified which proved to be the dorrigocin biosynthetic locus. Sequencing reads were assembled using the Phred-Phrap™ algorithm (University of Washington, Seattle, USA) recreating the entire DNA sequence of the cosmid insert. Reiterations of hybridizations of the large insert library with probes derived from the ends of the original cosmid allowed extension of sequence information on both sides of the original cosmid sequence until the complete gene cluster was obtained. The structure of dorrigocin suggests that it would be synthesized by a modular type I polyketide synthases (PKSs) containing 10 modules. It is notable that the PKS locus encoding dorrigocin/migrastatin would not have been detected by standard hybridization methods using probes generally used to isolate PKS genes, as the PKS genes of the locus are sufficiently divergent to preclude detection by those methods.

Three overlapping cosmid clones that were detected by the oligonucleotide probe derived from the GSTs remotely related to type I PKSs have been completely sequenced to provide approximately 54 Kb of DNA comprising the dorrigocin biosynthetic locus which is described in co-pending U.S. Ser. No. 10/132,134.

Example 7

Identification of a PhiC31-like Prophage in Streptomyces aizunensis NRRL B-11277

Streptomyces aizunensis NRRL B-11277 was obtained from the Agricultural Research Service collection (ARS) and cultured according to standard microbiological techniques (Hopwood). Unless otherwise stated, all subsequent experimental procedures were performed as described in the above examples.

A total of 462 GSTs were generated and analyzed by sequence comparison. Three GSTs derived from the small insert library showed similarity to genes from the actinophage phiC31 (Smith et al., The complete genome sequence of the Streptomyces temperate phage phiC31: evolutionary relationships to other viruses, 1999, Nucleic Acids Research 27 (10): 2145–2155) as shown in Table 14.

TABLE 14

| | Length (bp) | Proposed function | Homology | Probability | Proposed function of protein match |
|---|---|---|---|---|---|
| GST1 | 501 | terminase large subunit | CAA07103 | $2.00^{E}-66$ | phiC31 gp33; terminase, large subunit |
| GST2 | 501 | protease | CAA07105 | $7.00^{E}-41$ | phiC31 gp35; protease |
| GST3 | 501 | primase/helicase | CAA07134 | $1.00^{E}-58$ | phiC31 gp9a; primase/helicase |

Prophages are integrated versions of the genome of bacterial viruses and hence represent a type of gene cluster; that is, they include a collection of closely linked genes whose function is to propagate progeny virions. Oligonucleotide probes based on the three GSTs and probed a S. aizunensis large insert library were designed.

Several positive cosmid clones were identified and among these two non-overlapping clones were selected for further sequencing analysis. Cosmid 1 consisted of a 35 kb insert that included the sequences of both GST 1 and GST 2. Interestingly, the GST1 and GST 2 sequences (in the context of the insert of cosmid 1) were flanked by sequences encoding several other phiC31-like genes, and most notably these include the "late" genes of phiC31. Cosmid 1 also included a short sequence with significant similarity to the Cos sites of phage phiC31 and contained tRNA sequences in close proximity to this Cos-site-like element. Cosmid 2 consisted of an insert of at least 32 kb that included the sequences of GST 3. As expected, the GST 3 sequences (in the context of the insert of cosmid 2) were flanked by sequences encoding several other phiC31-like genes, and most notably these include the "early" genes of phiC31. Thus, a phiC31-like prophage was identified within the genome of S. aizunensis.

It is to be understood that the embodiments described herein are for illustrative purposes only and that various modifications or changes in light thereof will be suggested to the person skilled in the art and are to be included within the spirit and purview of this application and scope of the appended claims. All publications, patents and patent applications cited herein are hereby incorporated by reference in their entirety for all purposes.

The invention claimed is:

1. A high throughput method for identifying a gene or gene cluster involved in the biosynthesis of a prokaryotic microbial secondary metabolite natural product comprising:
   a) preparing, from isolated genomic DNA, a random small insert library comprised of DNA fragments of the genomic DNA and a random large insert library comprised of DNA fragments of the genomic DNA, wherein said small insert library has inserts smaller than said large insert library;
   b) determining the DNA sequence of at least part of a plurality of the fragments in the small insert library to form a plurality of Gene Sequence Tags (GSTs);
   c) comparing, under computer control, the DNA sequence of the GSTs or the amino acid sequence encoded by the DNA sequence of the GSTs with sequences in a database containing genes, gene fragments, DNA or amino acid sequences known to be involved in the biosynthesis of microbial secondary metabolite natural products to identify a GST that has sequence homology, as evidenced by an E value of $10^{-5}$ or lower, to a gene, gene fragment, DNA or amino acid sequence known to be involved in the biosynthesis of microbial secondary metabolite natural products; and
   d) hybridizing a nucleic acid probe comprising a sequence generated using the sequence of said GST identified in (c) to said large insert library to identify a DNA fragment from the large insert library, which DNA fragment contains the GST and a gene or gene cluster involved in the biosynthesis of a prokaryotic microbial secondary metabolite natural product.

2. The method according to claim 1 wherein the method identifies the microorganism from which the genomic DNA was obtained as a potential producer of the secondary metabolite natural product biosynthesis of which involves the gene cluster identified.

3. The method according to claim 1 wherein the gene or gene cluster is involved in the biosynthesis of an enediyne.

4. The method according to claim 1 wherein the gene or gene cluster is involved in the biosynthesis of a lipopeptide.

5. The method according to claim 1 wherein the gene or gene cluster is involved in the biosynthesis of a microbial natural product is a macrolide.

6. The method according to claim 1 wherein the gene or gene cluster is a polyketide synthase gene or a cluster of genes including a polyketide synthase gene.

7. The method according to claim 6 wherein the polyketide synthase gene is a modular Type 1 polyketide synthase gene.

8. The method according to claim 1 wherein the gene or gene cluster is involved in the biosynthesis of an orthosomycin compound.

9. The method of claim 8 wherein the orthosomycin is an everninomicin compound or an avilamycin compound.

10. The method according to claim 1 wherein the gene or gene cluster is involved in the biosynthesis of a glycosylated lipopeptide or an acidic lipopeptide.

11. The method according to claim 1 wherein the gene or gene cluster is involved in the biosynthesis of a benzodiazepine compound.

12. The method of claim 1, wherein said microbial secondary metabolite natural product is from a genus selected from *Nocardia, Geodermatophilus, Actinoplanes, Micromonospora, Nocardioides, Saccharothrix, Amycolatopsis, Kutzneria, Saccharomonospora, Saccharopolyspora, Kitasatospora, Streptomyces, Microbispora, Streptosporangium,* and *Actinomadura*.

13. The method of claim 1 wherein said GST identified in step (c) has sequence homology, as evidenced by an E value of $10^{-5}$ to $10^{-108}$, to a gene, gene fragment, DNA or amino acid sequence known to be involved in the biosynthesis.

14. The method of claim 1 wherein said GST identified in step (c) has sequence homology, as evidenced by an E value of $10^{-10}$ to $10^{-101}$, to a gene, gene fragment, DNA or amino acid sequence known to be involved in the biosynthesis.

15. The method of claim 1 wherein said GST identified in step (c) has sequence homology, as evidenced by an E value of $10^{-15}$ to $10^{-81}$, to a gene, gene fragment, DNA or amino acid sequence known to be involved in the biosynthesis.

16. The method of claim 1 wherein the GST identified in step (c) encodes a fragment of a sugar dehydratase.

17. The method of claim 1 wherein the GST identified in step (c) encodes a fragment of a sugar synthase.

18. The method of claim 1 wherein inserts in said small insert library are from 1.5 to 3.0 kb in length, inclusive.

19. The method of claim 1 wherein inserts in said large insert library are at least 30 kb in length.

* * * * *